(12) United States Patent
Ashley et al.

(10) Patent No.: US 7,855,192 B2
(45) Date of Patent: Dec. 21, 2010

(54) MACROLACTAMS BY ENGINEERED BIOSYNTHESIS

(75) Inventors: Gary W. Ashley, Alameda, CA (US); Hugo Menzella, Castro Valley, CA (US); Janice Lau Wee, San Mateo, CA (US); John R. Carney, Foster City, CA (US)

(73) Assignee: Kosan Biosciences, Inc., Princeton, NJ (US)

( * ) Notice: Subject to any disclaimer, the term of this patent is extended or adjusted under 35 U.S.C. 154(b) by 269 days.

(21) Appl. No.: 12/011,068

(22) Filed: Jan. 23, 2008

(65) Prior Publication Data

US 2008/0188450 A1 Aug. 7, 2008

Related U.S. Application Data

(60) Provisional application No. 60/897,727, filed on Jan. 26, 2007.

(51) Int. Cl.
C07D 225/06 (2006.01)
A61K 31/395 (2006.01)
A61P 35/00 (2006.01)

(52) U.S. Cl. ................................. 514/183; 540/461
(58) Field of Classification Search ............... 540/461; 514/183
See application file for complete search history.

(56) References Cited

U.S. PATENT DOCUMENTS

| | | | |
|---|---|---|---|
| 3,987,035 | A | 10/1976 | Rinehart |
| 4,261,989 | A | 4/1981 | Sasaki |
| 4,421,688 | A | 12/1983 | Muroi |
| 5,387,584 | A | 2/1995 | Schnur |
| 5,932,566 | A | 8/1999 | Schnur |
| 6,682,758 | B1 | 1/2004 | Tabibi |
| 6,872,715 | B2 | 3/2005 | Santi |
| 6,890,917 | B2 | 5/2005 | Snader |
| 7,282,493 | B2 | 10/2007 | Adams |
| 2004/0077058 | A1 | 4/2004 | Hutchinson |
| 2005/0026894 | A1 | 2/2005 | Tian |
| 2005/0256097 | A1 | 11/2005 | Zhong |
| 2006/0014730 | A1 | 1/2006 | Ulm |
| 2006/0067953 | A1 | 3/2006 | Mansfield |
| 2006/0148776 | A1 | 7/2006 | Ulm |
| 2006/0205705 | A1 | 9/2006 | Ross |
| 2007/0203110 | A1 | 8/2007 | Licari |

FOREIGN PATENT DOCUMENTS

| | | | |
|---|---|---|---|
| JP | 57-163369 A | | 3/1981 |
| WO | WO 93/14215 A1 | | 7/1993 |
| WO | 2005061461 | * | 7/2005 |
| WO | WO 2006/034147 A2 | | 3/2006 |
| WO | WO 2006/094029 A2 | | 9/2006 |
| WO | WO 2007/001049 A1 | | 1/2007 |
| WO | WO 2007/128829 A2 | | 11/2007 |
| WO | WO2008/056188 A2 | | 5/2008 |

OTHER PUBLICATIONS

Guo et al., Molec. Pharmacol. (2006) 70:1194-1203.
Staunton et al., Natural Products Reports (2001) 18:380-416.
Gooljarsingh et al., Proc. Natl. Acad. Sci. USA (2006) 103:7625-30.
Tao et al., 96th Annual AACR Meeting Abstract #1435, (2005).
Rascher et al., Appl. Environm. Microbiol. (2005) 71: 4862-71.
Maroney et al., Biochemistry (2006) 45: 5678-85.
Guo et al., Cancer Res. (2005) 65: 10006-15.
Kim et al., ChemBioChem (2007) 8: 1491-4.
Denis et al., Gene (1992) 111: 115-8.
Biermann et al., Gene (1992) 116: 43-9.
Schnur et al., J. Med. Chem. (1995) 38: 3806-12.
Schnur et al., J. Med. Chem. (1995) 38: 3813-20.
Kelland et al., J. Natl. Cancer Inst. (1999) 91: 1940-49.
Xiao et al., Mini-Reviews Med. Chem. (2006) 6: 1137-43.
Jez et al., Chem. Biol. (2003) 10: 361-8.
Patel et al., Chem. Biol. (2004) 11: 1625-33.
International Search Report and Written Opinion, PCT/US08/00918, May 23, 2008.
Hunziker, J.Am.Chem.Soc. (1998) 120: 1092-3.
Tsvetkov, Proc. Natl. Acad. Sci. USA (2005) 102: 5535-40.
Isaacs, Camcer Cell (2003) 3: 213-7.
Hunziker, D. et al., J. Am. Chem. Soc., vol. 120, pp. 1092-1093 (1998).
Isaacs, J. et al., Cancer Cell, vol. 3, pp. 213-217 (2003).
Tsvetkov, P. et al., Proc. Natl. Acad. Sci. USA, vol. 102, No. 15, pp. 5535-5540 (2005).

* cited by examiner

Primary Examiner—Bruck Kifle
(74) Attorney, Agent, or Firm—Elliott Korsen

(57) ABSTRACT

Macrolactams are made by feeding aromatic amino acids as replacement starter units to a mutant strain of the geldanamycin-producing microorganism *Streptomyces hygroscopicus* var. *geldanus* NRRL 3602, wherein the gene cluster encoding enzymes for the biosynthesis of the natural starter unit 3-amino-5-hydroxybenzoic acid has been deleted.

8 Claims, 7 Drawing Sheets

Figure 2:
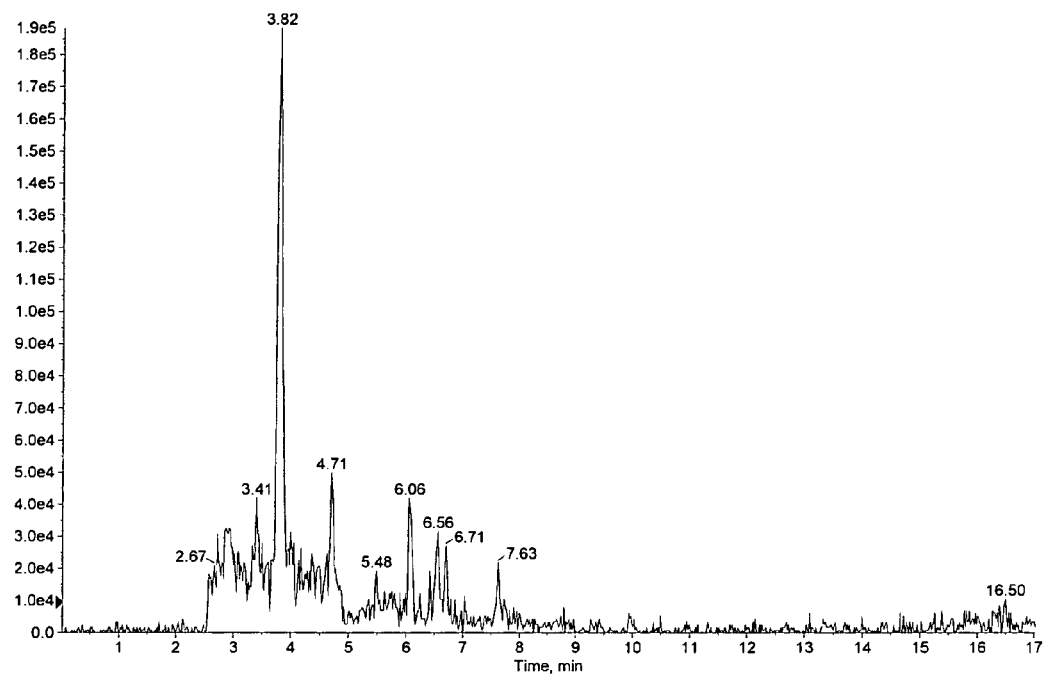

Fig. 1
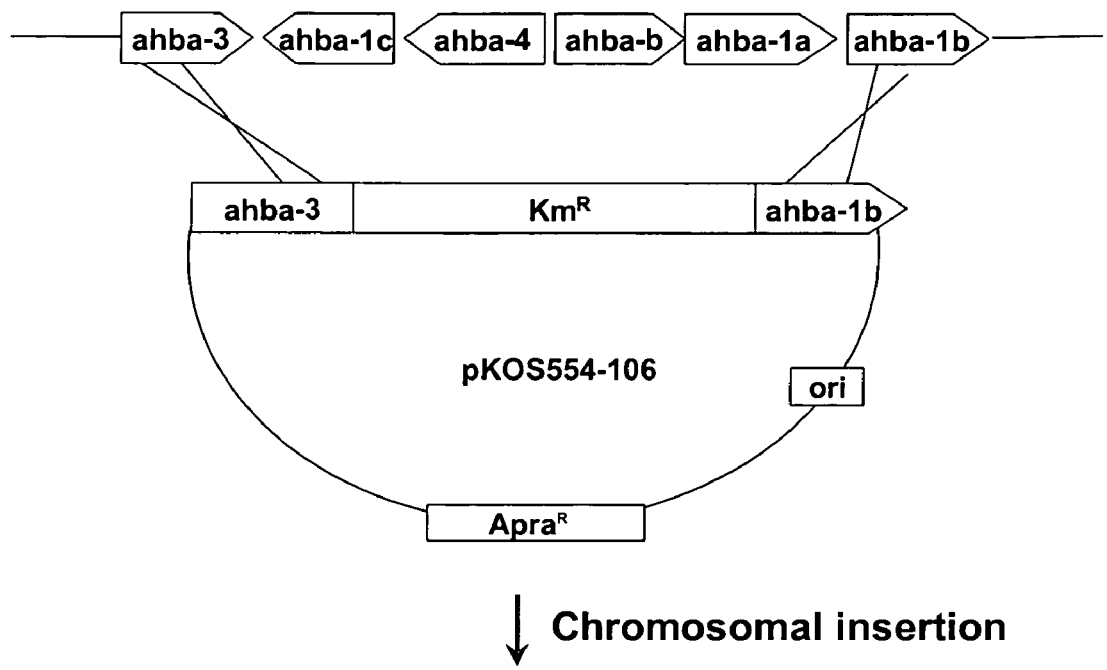
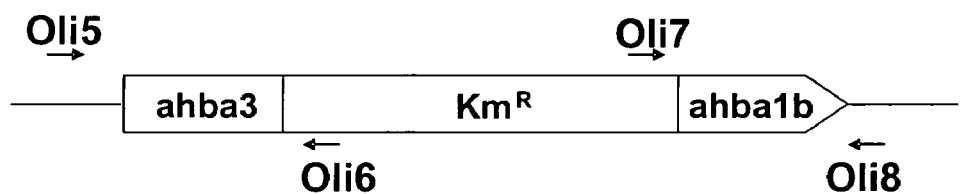

Strain K554-161 (no AHBA)

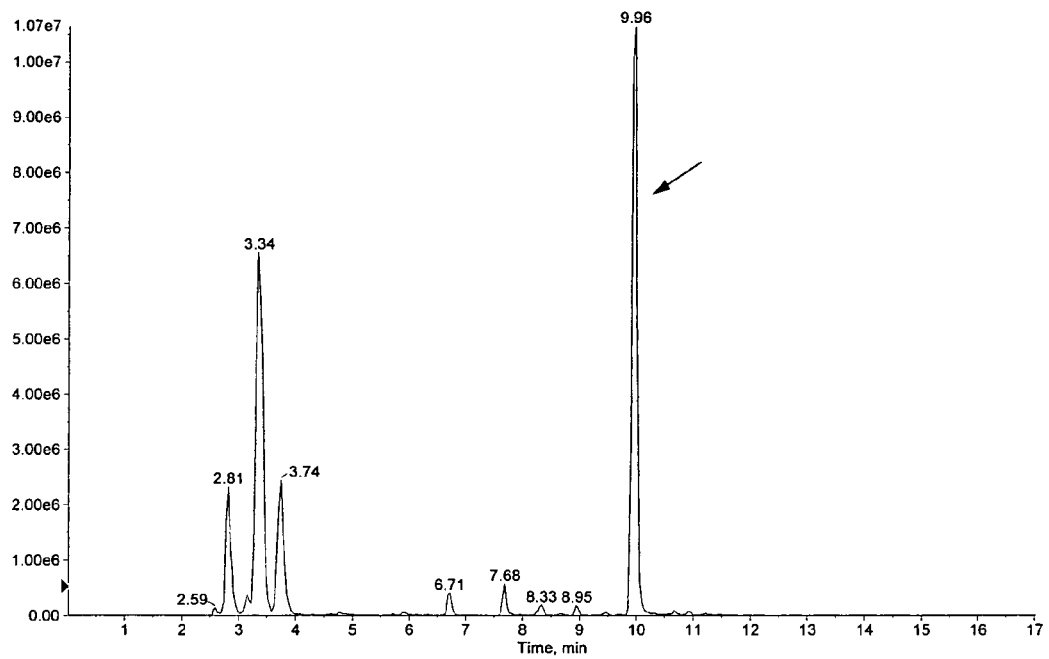
Fig. 3a Strain K554-161 (with 1 mM AHBA)

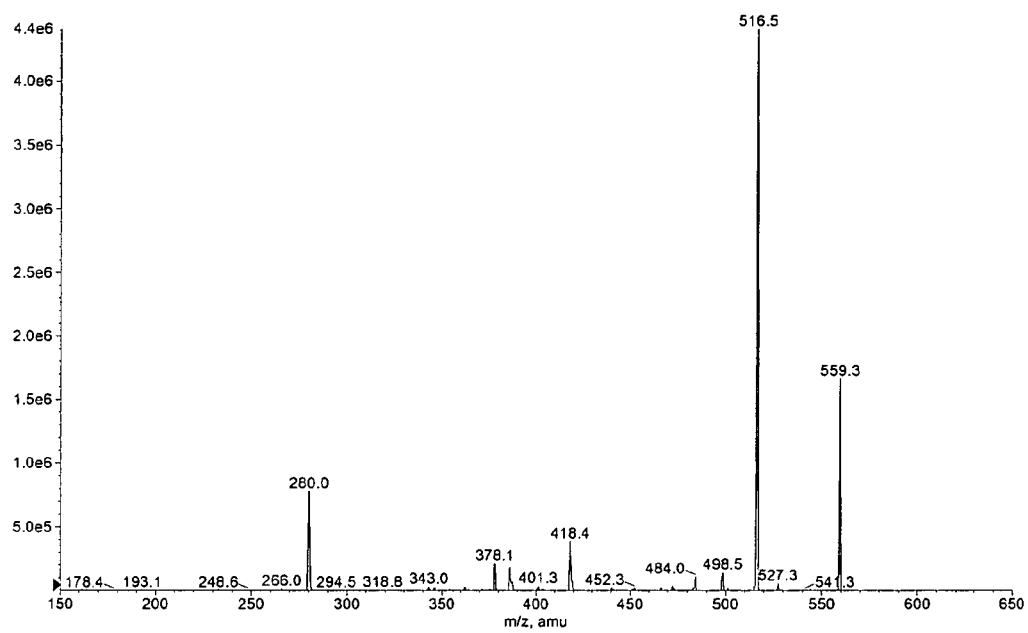
Fig. 3b   Strain K554-161 (with 1 mM AHBA)

Fig. 4a    *Streptomyces hygroscopicus* NRRL 3602
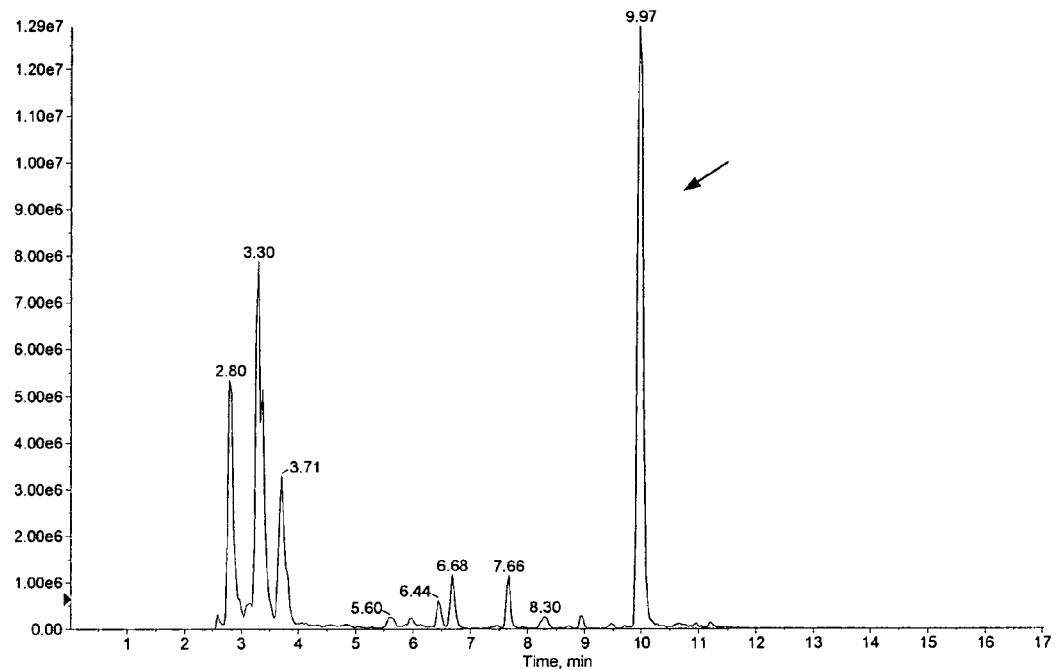

*Streptomyces hygroscopicus* NRRL 3602

MACROLACTAMS BY ENGINEERED BIOSYNTHESIS

CROSS-REFERENCE TO RELATED APPLICATIONS

This application claims the benefit under 35 U.S.C. §119(e) of U.S. Provisional Application No. 60/897,727, filed Jan. 26, 2007, the disclosure of which is incorporated herein by reference.

STATEMENT REGARDING FEDERALLY SPONSORED RESEARCH OR DEVELOPMENT

This invention was made with Government support under Grant No. 5 R44CA 096262-03, awarded by the National Institutes of Health. The Government has certain rights in this invention

BACKGROUND OF THE INVENTION

1. Field of the Invention

This invention relates to macrolactams having anti-tumor properties and methods for their preparation and use.

2. Description of Related Art

Geldanamycin belongs to the ansamycin natural product family, whose members are characterized by a macrolactam ring spanning two positions meta to each other on a benzoquinone, phenol or hydroquinone nucleus. Besides geldanamycin, the ansamycins include the macbecins, the herbimycins, the TAN-420s, and reblastatin.

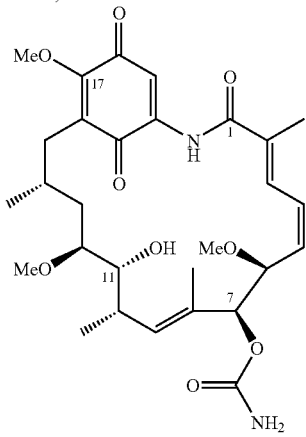

Geldanamycin

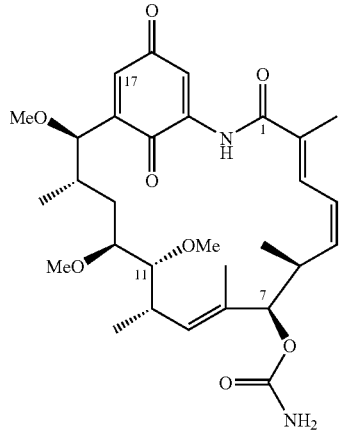

Macbecin I

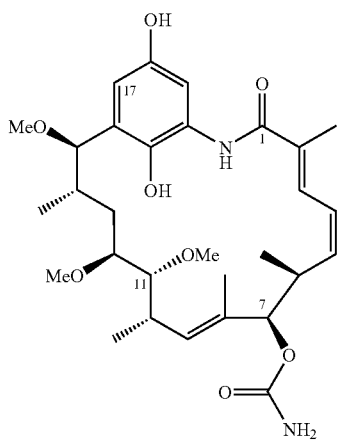

Macbecin II

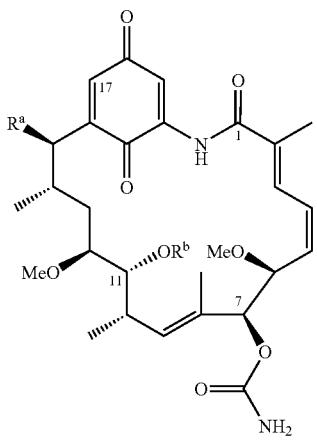

Herbimycin

A: $R^a$ = OMe  $R^b$ = Me
B: $R^a$ = H     $R^b$ = H
C: $R^a$ = OMe  $R^b$ = H

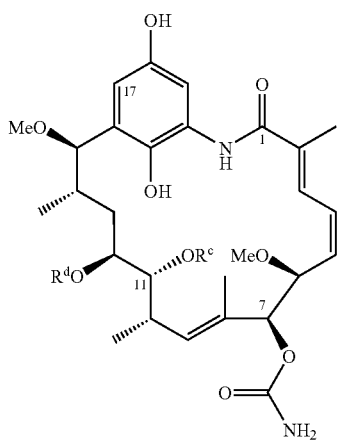

TAN-420

A: $R^c$ = H   $R^d$ = H
C: $R^c$ = H   $R^d$ = Me
E: $R^c$ = Me  $R^d$ = Me

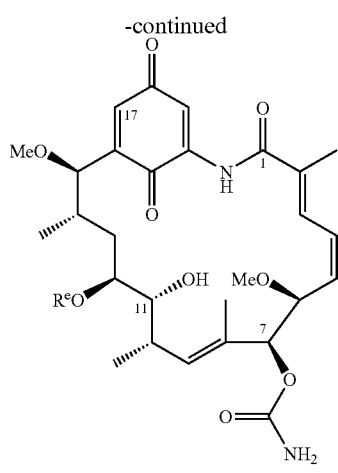

TAN-420

B: R$^e$ = H
D: R$^e$ = Me

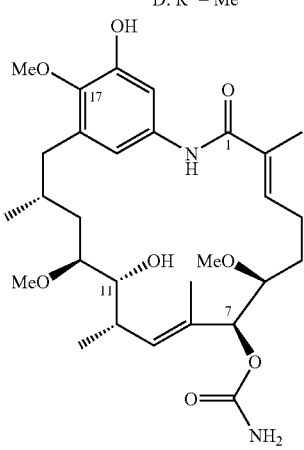

Reblastatin

Geldanamycin and its derivatives are the most extensively studied of the ansamycins. Although geldanamycin originally was identified as a result of screening for antibiotic activity, current interest in it derives from its potential as an anticancer agent. It is an inhibitor of heat shock protein-90 ("Hsp90"), a chaperone protein involved in the folding and activation of numerous "client proteins", including key proteins involved in signal transduction, cell cycle control and transcriptional regulation. The binding of an inhibitor to Hsp90 disrupts its interactions with a client protein, preventing the latter from being folded correctly with consequent loss of function or susceptibility to proteasome-mediated destruction. Among the Hsp90 client proteins are many mutated or overexpressed proteins implicated in cancer, such as mutant p53, Bcr-Abl kinase, Raf-1 kinase, Akt kinase, Npm-Alk kinase, Cdk4, Cdk6, Wee1, HER2/Neu (ErbB2), and HIF-1α. The possibility that multiple oncogenic client proteins can be simultaneously targeted has generated considerable interest in the development of Hsp90 inhibitors as anti-cancer drugs. See, e.g., Xiao et al., *Mini-Reviews Med. Chem.* 2006, 6 (10), 1137-1143.

Geldanamycin was considered for development as an anti-cancer drug, but its hepatotoxicity and poor bioavailability led to its withdrawal as a clinical candidate. Nevertheless, interest persists in the development of geldanamycin derivatives having Hsp90 inhibitory activity, but with an improved spectrum of pharmaceutical properties. C17 of geldanamycin has been an attractive focal point, chemically speaking, for the synthesis of geldanamycin derivatives because its methoxy group is readily displaced by a nucleophile, providing a convenient synthetic pathway to the 17-substituted-17-demethoxygeldanamycins. Structure-activity relationship ("SAR") studies have shown that chemically and sterically diverse 17-substituents can be introduced without destroying antitumor activity. See, e.g., Sasaki et al., U.S. Pat. No. 4,261,989 (1981) (hereinafter "Sasaki"); Schnur et al., U.S. Pat. No. 5,932,566 (1999); Schnur et al., *J. Med. Chem.* 1995, 38 (19), 3806-3812; Schnur et al., *J. Med. Chem.* 1995, 38 (19), 3813-3820; and Santi et al., U.S. Pat. No. 6,872,715 B2 (2005); the disclosures of which are incorporated by reference. The SAR inferences are supported by the X-ray crystal co-structure of the complex between Hsp90 and a geldanamycin derivative, showing that the 17-substituent juts out from the binding pocket and into the solvent (Jez et al., *Chemistry & Biology* 2003, 10, 361-368). The best-known 17-substituted geldanamycin derivatives are 17-allylamino-17-demethoxygeldanamycin (also known as 17-AAG or tanespimycin, Sasaki, supra) and 17-(2-dimethylaminoethyl)amino-17-demethoxygeldanamycin (also known as 17-DMAG or alvespimycin, Snader et al., U.S. Pat. No. 6,890,917 B2 (2005)), both of which are currently undergoing clinical trials.

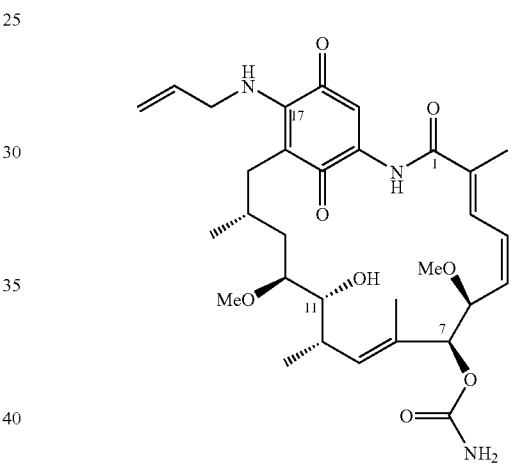

17-AAG

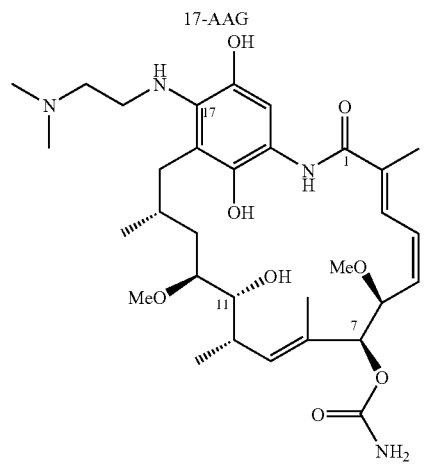

17-DMAG

It is desirable to develop additional ansamycin therapeutic agents, based on a structural motif other than 17-methoxy substitution in geldanamycin and having the potential for a more attractive spectrum of properties. One possible motif is represented by ansamycins having a non-benzoquinone aromatic nucleus. As noted above, some such ansamycins are naturally occurring: Macbecin II, the herbimycins, TAN420B, TAN420D, and reblastatin. Some semi-synthetic compounds having this motif also have been reported: Rinehart, Jr., et al., U.S. Pat. No. 3,987,035 (1976); Muroi et al., U.S. Pat. No. 4,421,688 (1983); Schnur, U.S. Pat. No. 5,387,584 (1995); Cullen et al., WO 93/14215 A1 (1993); Sasaki et al., JP 57-163369A (1982); and Yamaguchi et al., WO 2007/001049 A1 (2007); the disclosures of which are incorporated by reference. However, for various reasons non-benzoquinone ansamycins have progressed as drug candidates, with one possible exception as discussed infra.

BRIEF SUMMARY OF THE INVENTION

Herein, we disclose novel macrolactams capable of acting as Hsp90 inhibitors. These macrolactams are structurally related to the naturally occurring ansamycins and are derived biosynthetically by culturing a mutant strain of the geldanamycin-producing organism *Streptomyces hygroscopicus* var. *geldanus* NRRL 3602 (often referred to in the literature simply as *Streptomyces hygroscopicus* NRRL 3602). The mutant strain is incapable of making 3-amino-5-hydroxybenzoic acid ("AHBA"), the first substrate (or starter unit) in the biosynthetic pathway for geldanamycin, but otherwise contains an intact geldanamycin biosynthesis gene cluster. When supplied with unnatural replacement starter units (that is, aromatic amino acids other than AHBA), the mutant strain incorporates them into novel macrolactams. In particular, we have constructed a mutant strain, referred to herein as strain K554-161, in which the ahba-b gene cluster responsible for the biosynthesis of AHBA has been deleted, but without otherwise disrupting the gene cluster for geldanamycin biosynthesis.

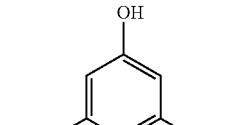

3-Amino-5-hydroxy-benzoic acid (AHBA)

Thus, in one embodiment, the present invention provides a macrolactam having a structure represented by formula I

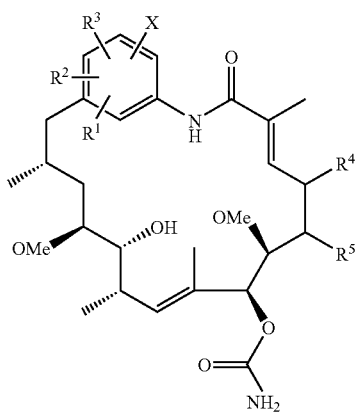

(I)

where

X is H, Cl, F, or OMe;

$R^1$, $R^2$, and $R^3$ are independently H or OH; and $R^4$ and $R^5$ are each H or combine to form a bond;

with the provisos that (i) at least one of $R^1$, $R^2$, and $R^3$ is H and (ii) the moiety

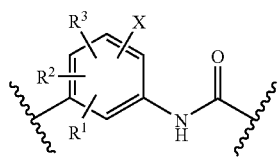

is other than

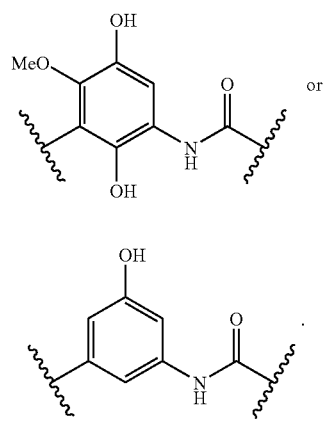

In another preferred embodiment, $R^4$ and $R^5$ are each H, corresponding to a macrolactam having a structure represented by formula I-a:

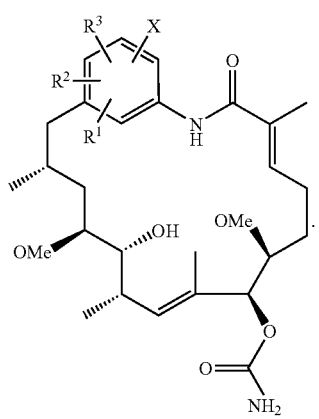

(I-a)

In another preferred embodiment, $R^4$ and $R^5$ combine to form a bond, corresponding to a macrolactam having a structure represented by formula I-b:

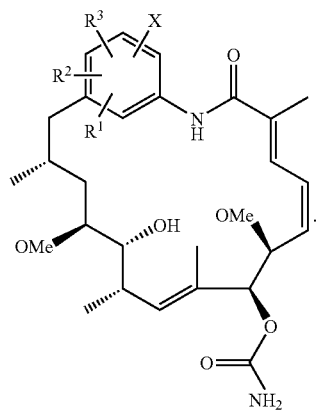

(I-b)

In one embodiment, X is Cl or F in formula I, I-a, or I-b. In another embodiment, X is H in formula I, I-a, or I-b. In yet another embodiment, X is OMe in formula I, I-a, or I-b.

In another embodiment, there is provided a method for preparing a macrolactam having a structure represented by formula I-c

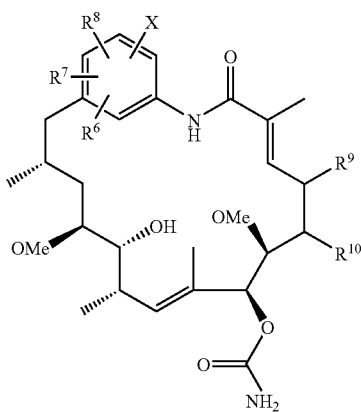

(I-c)

comprising the steps of
(a) adding (as a replacement starter unit) a compound having a structure represented by formula II or II-a

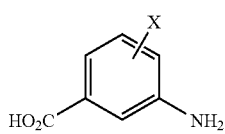

(II)

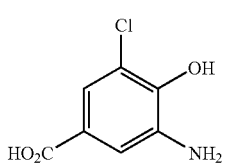

(II-a)

to a culture of a strain of *Streptomyces hygroscopicus* var. *geldanus* NRRL 3602 that is incapable of producing 3-amino-5-hydroxybenzoic acid but which contains an intact gene cluster for the synthesis of geldanamycin (preferably the strain is strain K554-161), and
(b) fermenting said culture under conditions in which a compound having a structure represented by formula I-c is produced;

wherein
X is H, Cl, F, or OMe;
$R^6$, $R^7$, and $R^8$ are independently H or OH; and
$R^9$ and $R^{10}$ are each H or combine to form a bond;
with the proviso that a least one of $R^6$, $R^7$, and $R^8$ is H.

In a preferred embodiment of the foregoing method, the compound added in step (a) has a structure according to formula II. In another preferred embodiment, the added compound has a structure according to formula II-a.

In one preferred embodiment, X is Cl or F in formulae I, Ia, Ib, Ic, or II. In another preferred embodiment, X is H in formulae I, Ia, Ib, Ic, or II.

In another embodiment, there is provided a method for treating a hyperproliferative disease in a patient suffering from said disease, comprising administering to said patient a therapeutically effective amount of a macrolactam of this invention. Preferably, the hyperproliferative disease so treated is breast cancer, ovarian cancer, leukemia, colon cancer, or lung cancer.

In another embodiment, there is provided a pharmaceutical composition comprising a macrolactam of this invention and a pharmaceutically acceptable excipient.

In another embodiment, there is provided a method for inhibiting the proliferation of a target cell, comprising contacting the target cell with an effective amount of a macrolactam according to this invention. Preferably, the target cell so inhibited is a breast cancer, ovarian cancer, leukemia, colon cancer, or lung cancer cell. Generally, the effective amount will correspond to a concentration of between about 40 and about 10,000 nM, more preferably between about 40 and about 900 nM of the macrolactam.

BRIEF DESCRIPTION OF THE DRAWING(S)

FIG. 1 illustrates conceptually the production of strain K554-161 by the deletion of the ahba-b gene cluster of *S. hygroscopicus* NRRL 3602.

Figure 4B:
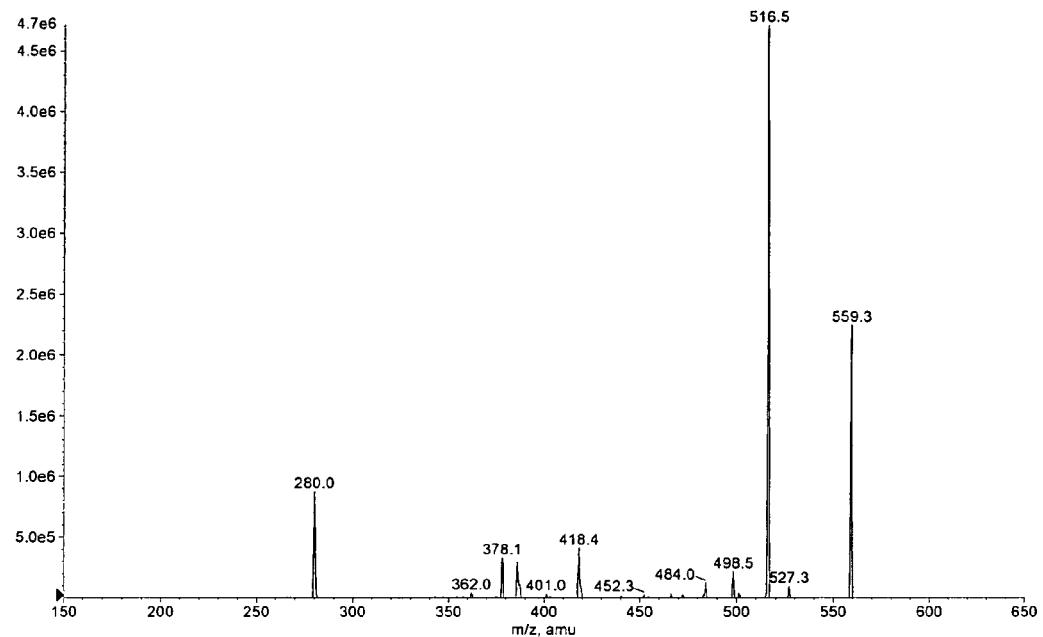

FIG. 2 is an LC-MS trace of the product isolate from a fermentation of strain K554-161 without any AHBA added. FIG. 3a is the LC-MS trace of the product isolate when the same strain is fermented in the presence of 1 mM AHBA. FIG. 3b is the mass spectrum of the material eluting at 9.96 min from the LC-MS trace of FIG. 3a. FIGS. 4a and 4b are a comparative LP-MS trace and a comparative mass spectrum, respectively, for the product isolate from a fermentation of the geldanamycin producing strain *S. hygroscopicus* var. *geldanus* NRRL 3602.

Figure 5:
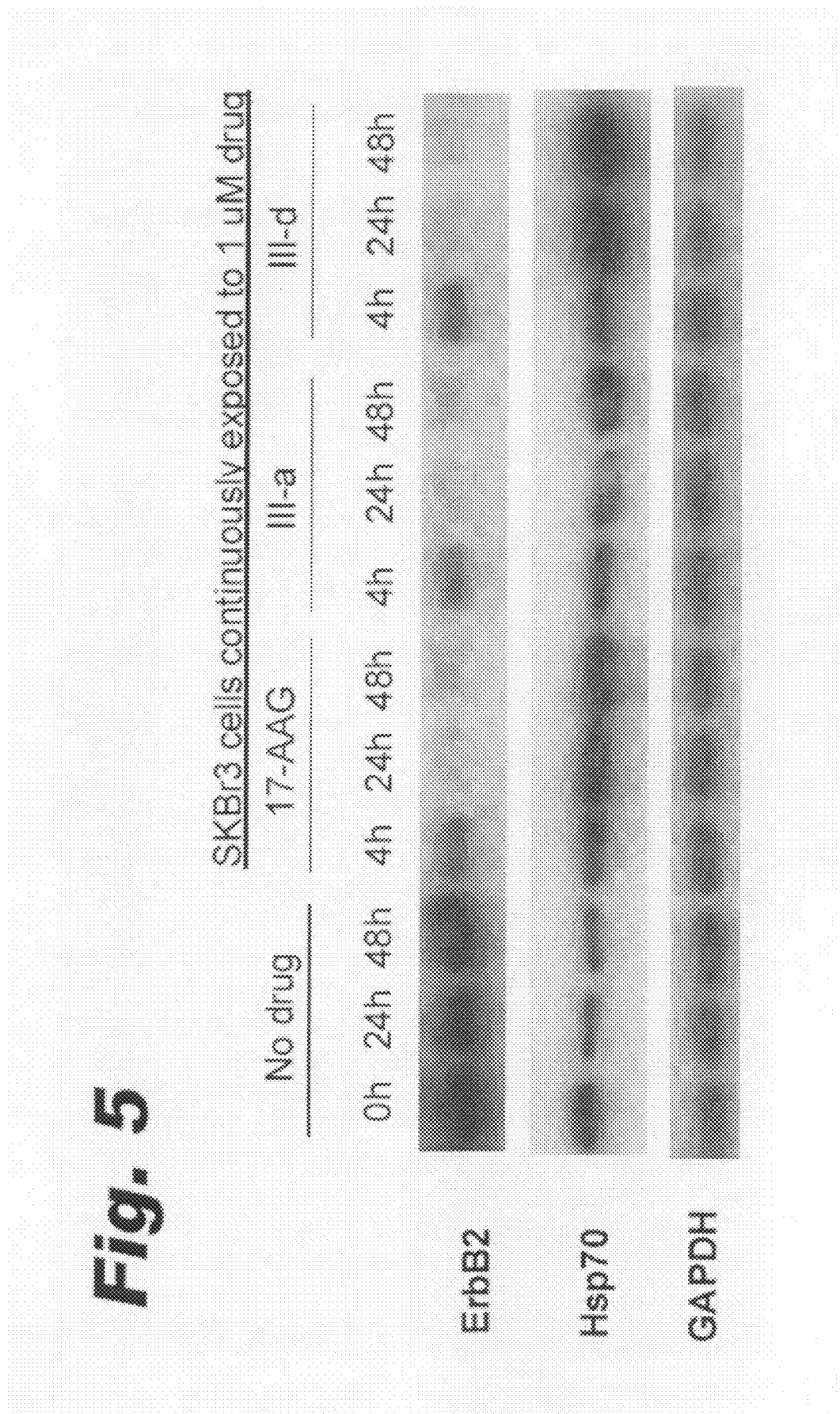

FIG. 5 shows the effect of exposure to macrolactams of this invention on the concentrations of an Hsp90 client protein and a protein induced upon inhibition of Hsp90.

DETAILED DESCRIPTION OF THE INVENTION

Geldanamycin and the other ansamycins are members of the polyketide superfamily of natural products. Polyketides are related not so much by their structures, which vary enormously, but, rather, by their biosynthesis, which are mediated by enzymes referred to as polyketide synthases ("PKSs").

Geldanamycin PKS is a Type I (or modular) PKS, characterized by large multifunctional enzymes divided into modules of activity arranged in assembly-line fashion. Each module has a number of enzymatic activities ("domains") that load, activate, and condense a two-carbon (ketide) unit to a growing polyketide chain and may have additional modifying domains that chemically alter (reduce, dehydrate, etc.) the just-added ketide unit. The number and order of modules and the types of modifying domains (if any) contained in each module determine the basic structure of the resulting polyketide. For a general review on PKSs, see Staunton et al., *Nat. Prod. Rep.* 2001, 18, 380-416.

Initiation of polyketide synthesis occurs at the loading module, comprising an acyltransferase ("AT") and an acyl carrier protein ("ACP") domain, where the first (or starter unit) of the polyketide is loaded onto the PKS via a high-energy thioester linkage. Subsequent modules ("extender modules") comprising ketosynthase ("KS"), AT, and ACP domains (collectively referred to as a minimal PKS module) load two-carbon malonate based extender units, again via thioester linkages. (The "two-carbon" phraseology refers to the polyketide main chain; the extender unit also may have carbon atoms destined for side chains, as in the case of a methyl malonyl extender unit.) The loaded extender unit condenses with the growing polyketide chain attached to the loading module or the immediately preceding extender module, as the case may be, in a Claisen reaction extending the polyketide chain by two carbons. If present, modifying domains such as a ketoreductase ("KR") domain, a dehydratase ("DH") domain, an enoylreductase ("ER") domain, and/or a methyl-transferase domain then operate on the just-added two-carbon unit and modify it by reduction, dehydration, etc. After the action of the last extender module, a release domain—typically a thioesterase or an amidase domain—releases the polyketide from the PKS, usually forming a lactone or lactam in the process by cyclizing the terminal acyl group with an upstream hydroxyl or amino group. Other enzymes (called "tailoring enzymes" or "modification enzymes") may further modify the polyketide, in what are referred to as post-PKS modifications. Tailoring enzymes can be, for example, oxygenases, glycosyl- and methyl-transferases, acyltransferases, halogenases, cyclases, aminotransferases, and hydroxylases.

Hutchinson et al., US 2004/0077058 A1 (2004), the disclosure of which is incorporated herein by reference, describes the geldanamycin PKS gene cluster and its cloning from *S. hygroscopicus* NRRL 3602. Geldanamycin PKS comprises a loading domain accepting AHBA as the starter unit and seven modules each adding an extender unit (malonyl, 2-methoxymalonyl, or 2-methymalonyl, depending on the module).

The initial product of the geldanamycin PKS is progeldanamycin, which is converted to geldanamycin via several tailoring enzyme-mediated steps: carbamoylation of the C7 hydroxyl group; hydroxylation of C17 and O-methylation of the hydroxyl group so introduced; hydroxylation and oxidation of C21; and dehydrogenation of C4-C5:

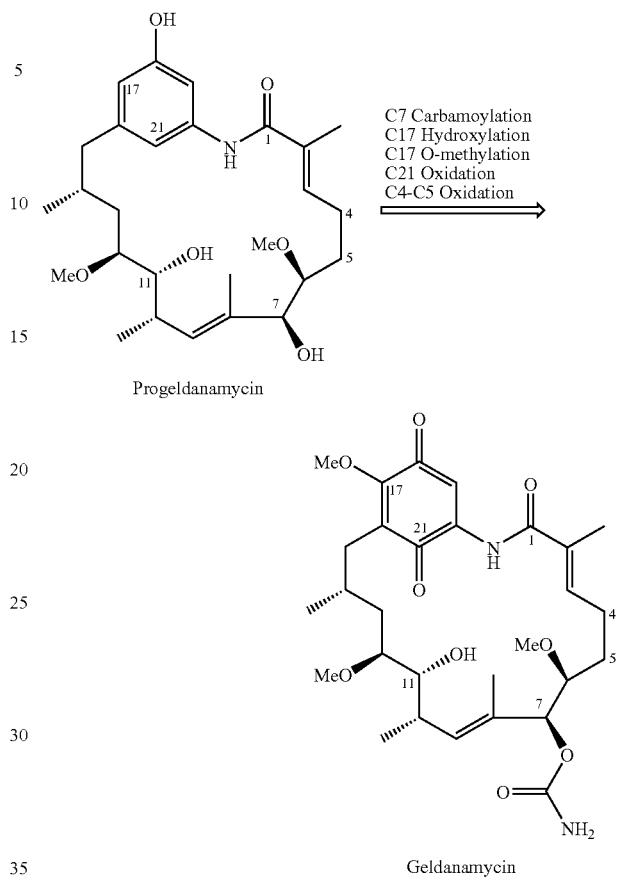

The geldanamycin biosynthetic pathway has been bioengineered to produce new geldanamycin analogs. Employing a technique known as "AT-swap", in which a native AT domain is replaced by an AT domain from a different PKS, Tian et al., US 2005/0026894 A1 (2005) (hereinafter "Tian") and Patel et al., *Chemistry & Biology* 2004, 11, 1625-1633 (hereinafter "Patel") prepared geldanamycin analogs characterized by, inter alia, the absence of a 2-methyl group and the suppression of the oxidation of the aromatic ring to the quinone oxidation state:

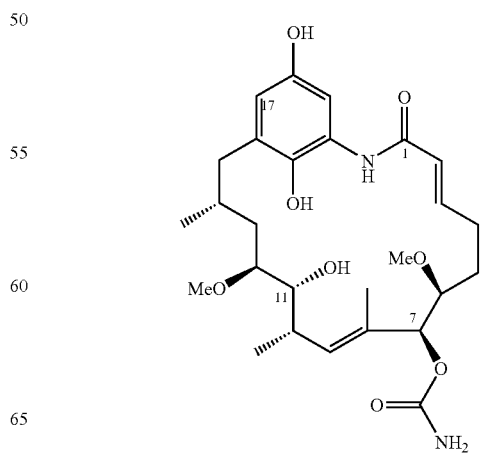

-continued

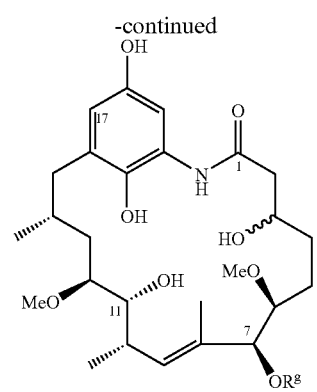

R<sup>g</sup> = CONH₂ or H

Tian also reported the use of these compounds as starting materials for chemical derivatization to prepare further geldanamycin analogs.

Rascher et al., *Applied Environmental Microbiology* 2005, 71 (8), 4862-4871 (hereinafter "Rascher") disclosed that disruption of the oxygenase gene gdmM resulted in the production of a geldanamycin analog (KOS-1806) in which both hydroxylation and oxidation of the aromatic ring and C4-C5 oxidation were suppressed.

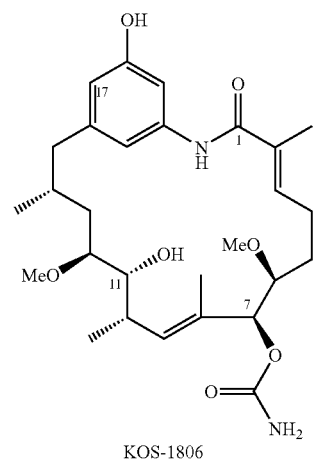

KOS-1806

Rascher also reported that, in another mutant strain (K390-76-1) in which the gene cluster (ahba-b) for AHBA formation was deleted, the production of geldanamycin was suppressed but was restorable by the feeding of AHBA.

After the claimed priority date for this application, Kim et al., *Chem Bio Chem* 2007, 8, 1491-1494, disclosed the inactivation of the AHBA synthase gene in *S. hygroscopicus* subsp. *duamyceticus* JCM4427, which is also a producer of geldanamycin. The resulting strain was grown in the presence of various amino- or hydroxy-benzoic acids. A number of metabolites attributed to incorporation of these benzoic acids were characterized by LC-MS.

Also after the claimed priority date of this application, Martin et al., WO 2007/122829 A2 (2007) disclosed the preparation of 18,21-didesoxymacbecin analogs by feeding non-natural starter units to a macbecin producing organism. Non-natural starter units disclosed include 3-aminobenzoic acid, 5-amino-2-fluorobenzoic acid, 5-amino-3-fluoro-benzoic acid, 5-amino-2,3-difluorobenzoic acid, and 5-amino-2,3,6-trifluorobenzoic acid.

We have created a new mutant strain of *S. hygroscopicus* NRRL 3602, which we have named strain K554-161, in which the ahba-b gene cluster has been deleted but which, when fed certain aromatic amino acids as replacement starter units, accepts them and produces novel macrolactams. (When fed AHBA, strain K554-161 produced geldanamycin, confirming that its geldanamycin PKS is intact.)

Among the preferred replacement starter units of formula II or II-a that can be fed to strain K554-161 to prepare macrolactams are:

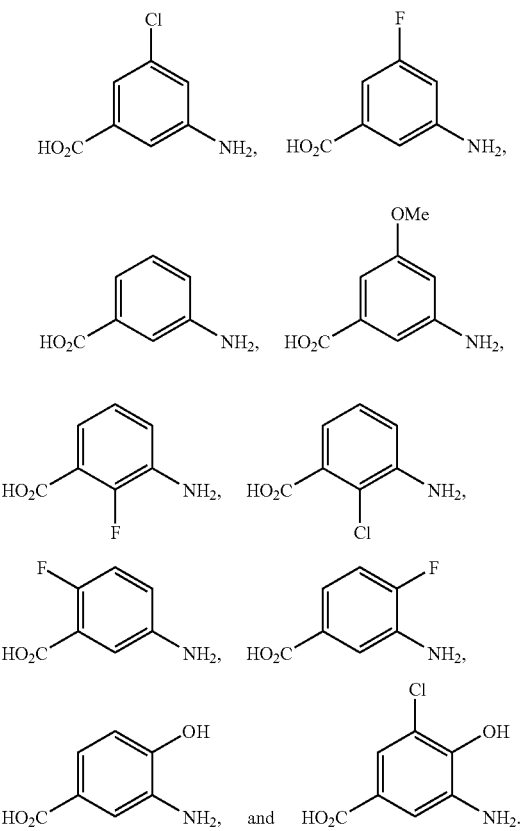

2-Chloro-5-aminobenzoic acid is not a particularly desirable substrate; its feeding resulted in dechlorination of the aromatic ring. Nor is 3-amino-2-hydroxybenzoic acid, which does not seem to be easily accepted by the producing organism to produce polyketide, a particularly desirable substrate.

Those skilled in the art will appreciate that these replacement starter units, being amino acids, can be used, handled, or added to the fermentation mixture in the form of a corresponding conjugate acid salt, such as a hydrochloride, a trifluoroacetate, and the like. Or, they can be used, handled, or added in the form of their carboxylic acid salts, such as a sodium or potassium salt. Of course, the zwitterionic form can also be so used, handled or added.

Macrolactams of formula I-a made by the method of this invention include those in which the moiety

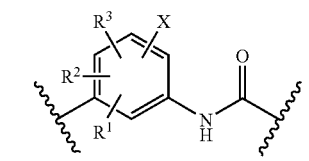
in formula I-a is selected from the group consisting of
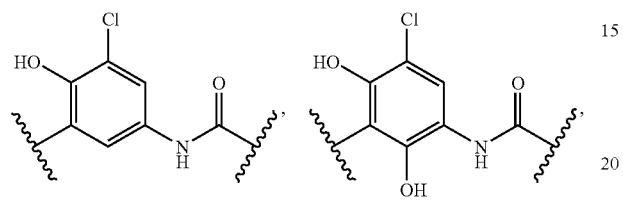
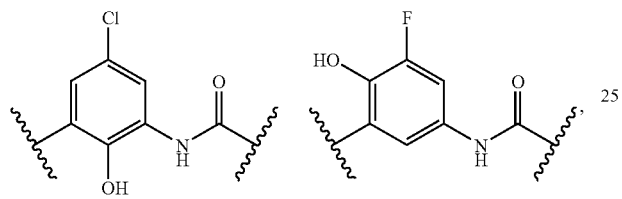
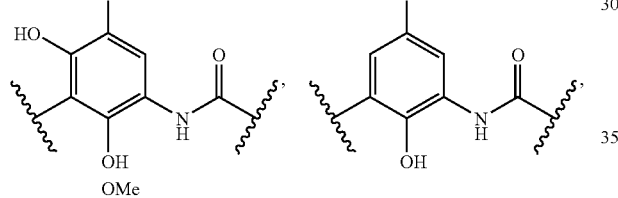
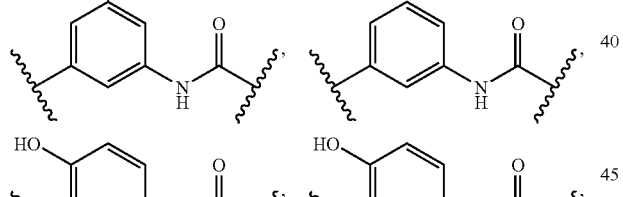
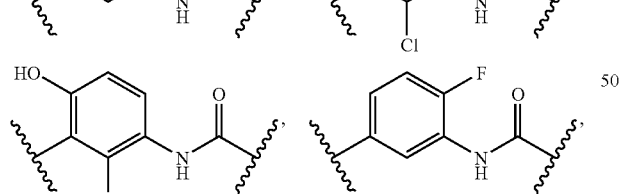
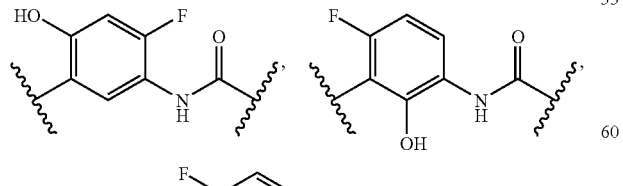
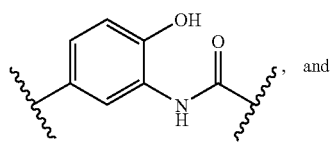, and
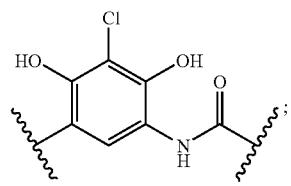;
corresponding respectively to compounds whose fully written-out structures are III-a through III-q.
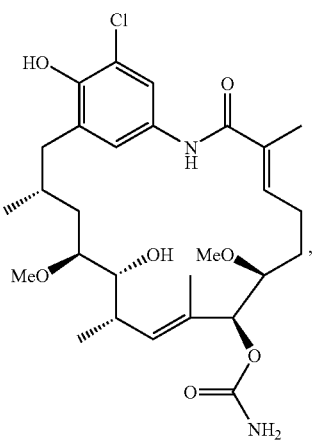
(III-a)
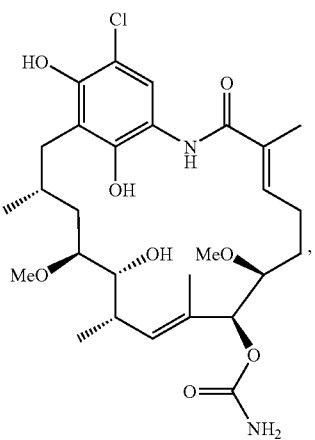
(III-b)

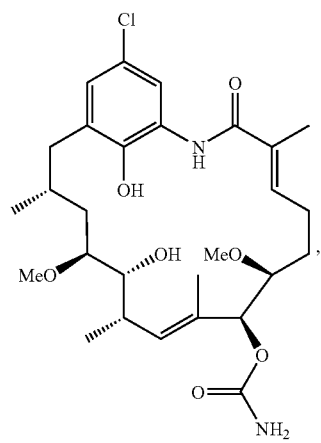
(III-c)
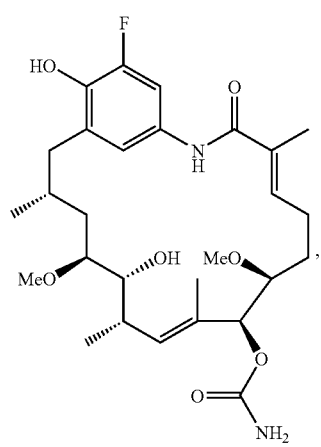
(III-d)
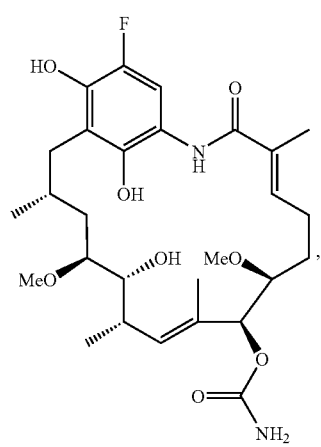
(III-e)
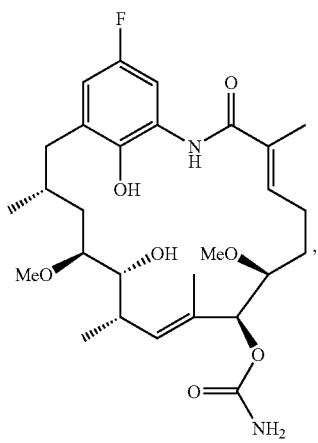
(III-f)
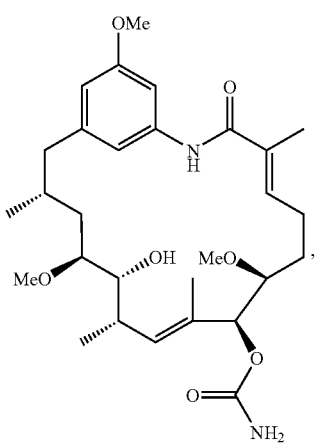
(III-g)
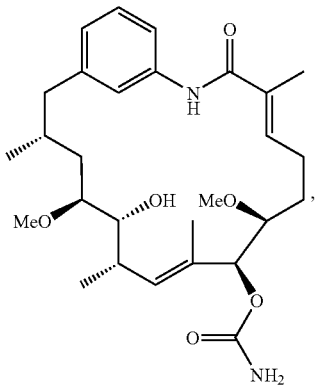
(III-h)

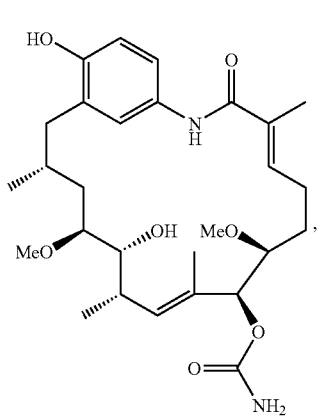
(III-i)
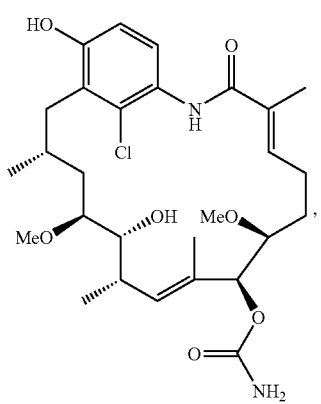
(III-j)
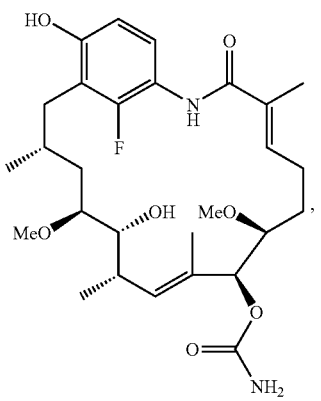
(III-k)
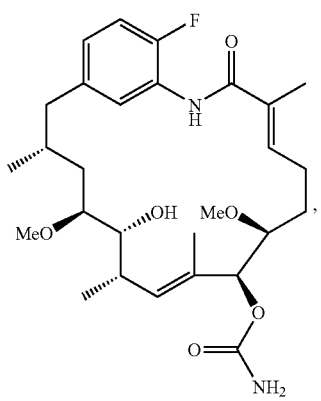
(III-l)
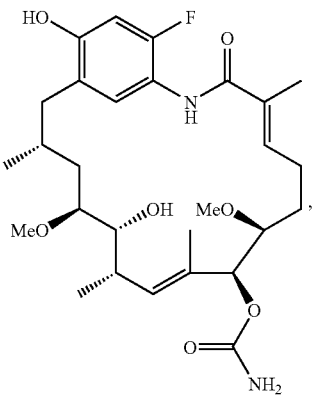
(III-m)
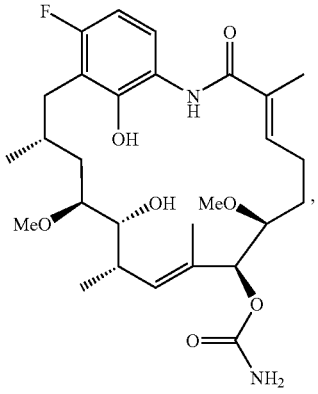
(III-n)
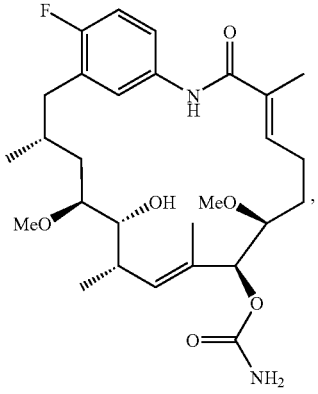
(III-o)
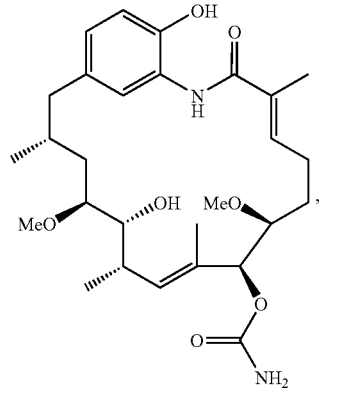
(III-p)
and -continued

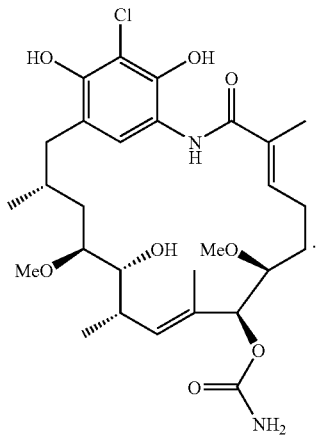
(III-q)

Among the above, compounds III-a and III-d are preferred.

The macrolactams produced by strain K554-161 tend to lack the C4-C5 double bond found in geldanamycin, as exemplified by compounds III-a through III-o. As the feeding of AHBA to strain K554-161 resulted in the production of geldanamycin, we surmise that the C4-C5 tailoring enzyme is active, but the compounds initially produced by the PKS using replacement starter units are inferior substrates for it. Also, the aromatic nuclei of the replacement starter units were not oxidized to the quinone oxidation state, although, in some instances, partial oxidation manifested by hydroxylation at C17 and/or C21 occurred.

As further evidence that the C4-C5 tailoring enzyme is intact, we have observed C4-C5 oxidation in several products isolated in minor amounts. Examples include compounds of formula IV-a, IV-b, IV-c, and IV-d from the feeding of 3-aminobenzoic acid, 3-amino-5-chlorobenzoic acid, 3-amino-5-fluorobenzoic acid, and 3-amino-4-hydroxybenzoic acid, respectively:

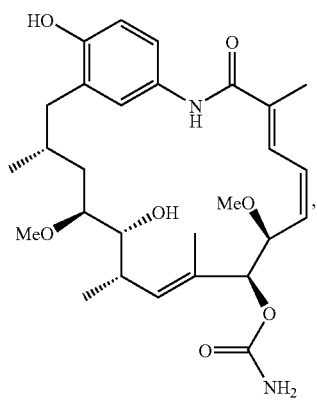
(IV-a)

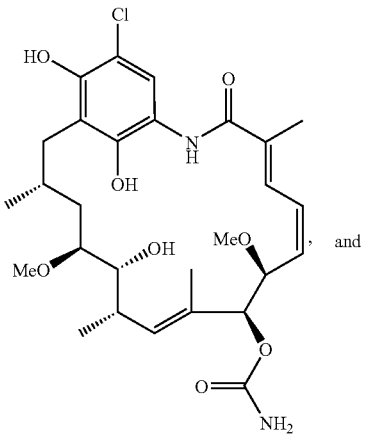
(IV-b)

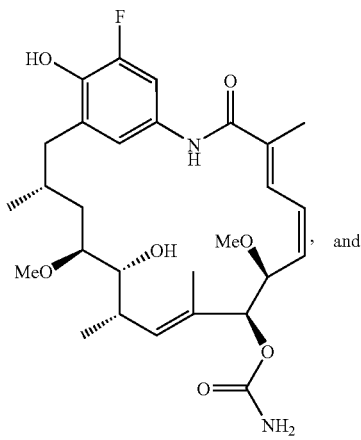
(IV-c)

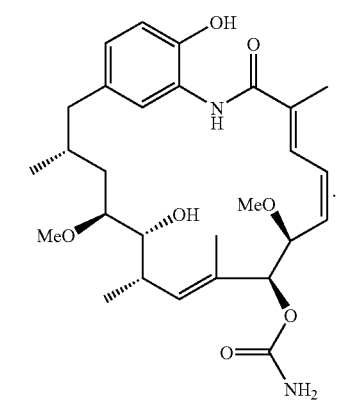
(IV-d)

Various studies have concluded that the reduction of the quinone group in the geldanamycin derivatives 17-AAG and 17-DMAG by the enzyme NAD(P)H:quinone oxido-reductase 1 (also referred to as NQO1 or DT diaphorase) to the corresponding hydroquinone forms (17-AAGH$_2$ and 17-DMAGH$_2$, respectively) is important to their activity as Hsp90 inhibitors. See Kelland et al., *J. Nat'l Cancer Inst.* 1999, 91 (22), 1940-1949; Guo et al., *Cancer Res.* 2005, 65 (21), 10006-10015; Guo et al., *Mol. Pharmacol.* 2006, 70 (4), 1194-1203; Maroney et al., *Biochemistry* 2006, 45, 5678-5685; and Gooljarsingh et al., *Proc. Nat'l Acad. Sci.* (*USA*), 2006, 103 (20), 7625-7630.

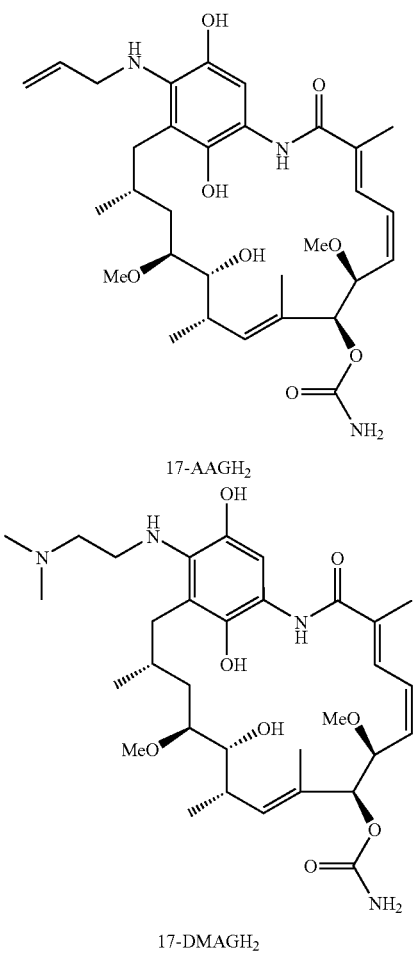

17-AAGH₂

17-DMAGH₂

These studies indicate that the reduced forms 17-AAGH₂ and 17-DMAGH₂ are more potent inhibitors of Hsp90 than the parent quinones. In one study, two breast cancer cell lines, isogenic except for one being transfected to express high levels of NQO1, were exposed to 17-AAG. 17-AAG was about 12 times more potent against the NQO1 expressing cell line than against the non-NQO1 expressing cell line. In another study, the hydroquinone forms were found to bind more tightly (by about 40-fold) to Hsp90 than the corresponding quinones and to have slower dissociation rates. Computer modeling calculations also predict that the binding of the hydroquinone form is energetically more favorable.

However, the hydroquinones of geldanamycin compounds are unstable, being readily oxidized back to the quinones in solution, especially in the presence of metal ions. Special precautions are needed to prevent oxidation, such as storing solutions in the presence of metal chelators, low pH buffers, and/or antioxidants. See, e.g., Adams et al., US U.S. Pat. No. 7,282,493 B2 (2007); and Ross et al., US 2006/0205705 A1 (2006). Thus, the use of the hydroquinones as therapeutic agents faces substantial formulation challenges. Nevertheless, a salt form of 17-AAGH₂ is undergoing clinical trials.

Unlike 17-AAG and 17-DMAG, the macrolactams of the present invention are not dependent upon reduction by NQO1 for enhancement of their Hsp90 inhibitory activity. Lacking a hydroquinone group, they do not require the special handling and storage precautions to prevent oxidation to the quinone form.

Compounds of this invention can be used to treat a variety of proliferative disorders, such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. More particularly, cancers that can be targeted for treatment include breast cancer, multiple myeloma, melanoma, colon cancer, lung cancer (especially non-small cell lung cancer (NSCLC)), prostate cancer, thyroid cancer, ovarian cancer, lymphoma, pancreatic cancer, and leukemia (especially chronic myelogenous leukemia (CML) and chronic lymphocytic leukemia or (CLL)).

Where a compound of this invention is used to inhibit the proliferation of a target cell, the target cell so inhibited preferably is a breast cancer, ovarian cancer, leukemia, colon cancer, or lung cancer cell. Generally, the effective inhibitory amount will correspond to a concentration of between about 40 and about 10,000 nM, more preferably between about 40 and about 900 nM of the macrolactam.

Non-cancer disorders that are characterized by cellular hyperproliferation can also be treated by compounds of this invention. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

Compounds of this invention can be administered in combination with another active pharmaceutical ingredient (API), such as other anti-cancer or cytotoxic agents including alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bortezomib, busulfan, callistatin A, camptothecin, capecitabine, CC-1065, cisplatin, cryptophycins, daunorubicin, disorazole, docetaxel, doxorubicin, duocarmycin, dynemycin A, epothilones, etoposide, floxuridine, fludarabine, fluorouracil, gefitinib, gemcitabine, hydroxyurea, imatinib, interferons, interleukins, irinotecan, maytansine, methotrexate, mitomycin C, oxaliplatin, paclitaxel, suberoylanilide hydroxamic acid (SAHA), thiotepa, topotecan, trichostatin A, vinblastine, vincristine, and vindesine. Preferred combinations are with gefitinib (Iressa®), bortezomib (Velcade®), paclitaxel (Taxol®), docetaxel, thalidomide (Thalomid®), lenalidomide (Revlimid®), and Herceptin®. In a combination treatment with another API, the other API can be administered separately, in its own formulation, or, where amenable, can be administered as an additional component added to a formulation of a compound of this invention.

Formulations of compounds of this invention may contain excipients, such as carriers, surface active agents, thickening or emulsifying agents, solid binders, dispersion or suspension aids, solubilizers, colorants, flavoring agents, coatings, cryoprotectants, lyoprotectants, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The subject with a compound of this invention is typically a human, although the invention can be practiced for veterinary purposes, with suitable adjustment of the unit dose, for the particular mammal of interest (including cats, cattle, dogs, horses, and the like).

A therapeutically effective amount of a compound of this invention that amount of such compound that elicits the biological or medicinal response in a cell culture, tissue system, animal, or human that is being sought by a researcher, veterinarian, clinician, or physician, which includes alleviation of the symptoms of the disease, condition, or disorder being treated. The dosage can range from about 4 mg/m$^2$ to about 4000 mg/m$^2$, depending on the frequency of administration.

Formulation techniques developed for use with ansamycins that can be used for the macrolactams of this invention include formulations based on triglycerides of various chain lengths (Ulm et al., US 2006/0014730 A1 (2006); Ulm et al., US 2006/0148776 A1 (2006); and Isaacs et al., WO 2006/094029 A2 (2006)), DMSO/lecithin combinations (Tabibi et al., U.S. Pat. No. 6,682,758 B1 (2004)); polyethoxylated castor oil (Zhong et al., US 2005/0256097 A1 (2005)); various solubilizers or dispersants (Mansfield et al., US 2006/0067953 A1 (2006); dimethylsorbide (Desai et al., WO 2006/034147 A2 (2006)); and nanoparticle suspensions (Tao et al., *Am. Assoc. Cancer Res.*, 96th Annual Meeting (Apr. 16-20, 2005), abstract no. 1435; Licari et al., US 2007/0203110 A1 (2007)); the disclosures of which are incorporated herein by reference.

The practice of this invention can be further understood by reference to the following examples, which are provided by way of illustration and not of limitation. Some of the replacement starter units are commercially available, so no synthetic procedure is provided for them. For the others, synthetic procedures are provided.

EXAMPLE 1

Preparation of Strain K554-161

General. The ahba-b gene cluster of *S. hygroscopicus* NRRL 3602 is separated by more than 30 kb from the geldanamycin (gdm) PKS genes and contains six ORFs encoding the enzymes for the synthesis of AHBA (Rascher, supra). Two DNA fragments of ca. 1 kb at the border of the cluster were PCR amplified and used as homology arms to flank a kanamycin resistance cassette derived from pFDneoS. The construction was inserted into the conjugative plasmid pKC1139, which contains an apramycin resistance marker and a thermosensitive replicon.

Mutant clones where the disruption cassette was inserted into the chromosome were selected by incubating the cultures at the restrictive temperature. Next, 200 colonies were screened for the kanamycin resistant/apramycin sensitive phenotype, expected for the double crossovers. Genetic analysis by PCR of the selected colonies was used to identify a clone (strain K554-161) where the six ORFs of the ahba-b gene cluster had been replaced by the kanamycin resistance cassette.

A sample of strain K554-161 has been deposited under accession number PTA-8002 with the American Type Culture Collection (ATCC), P.O. Box 1549, Manassas, Va. 20108, USA, according to the terms of the Budapest Treaty on Nov. 15, 2006.

Strains, media, and growth conditions. *S. hygroscopicus* var. *geldanus* NRRL 3602 was obtained from the Northern Regional Research Laboratory of the Agricultural Research Service. *Escherichia coli* XL1-blue (Strategene) were used for DNA manipulations. *E. coli* ET12657/pUZ8002 (Kieser et al., Practical *Streptomyces* Genetics (The John Innes Foundation, Norwich, U.K., 2000)) (hereinafter "Kieser") was used as a donor in *E. coli-S. hygroscopicus* conjugation. For propagation and sporulation, the *S. hygroscopicus* was grown on tomato paste agar at 28° C. for 14 days (Patel, supra). *E. coli* strains were grown on LB medium. The *S. hygroscopicus* strains were maintained as spore suspensions in 20% glycerol at −80° C.

Primers and PCR conditions. Primers Oli1 and Oli2 (Table 1) were used for the PCR amplification of the right homology arm containing a fragment of the gene ahba-3. Primers Oli3 and Oli4 were used for the amplification of the left homology arm containing a fragment of the gene ahba-1b (see FIG. 1). PCR amplifications were carried out using *S. hygroscopicus* genomic DNA as a template, prepared as described by Kieser, supra, and the PCR fail-safe kit (Epicentre) following the manufacturer's instructions.

TABLE 1

Oligonucleotides Used for Preparing Strain K554-161

| Primer | Sequence | Remarks |
|---|---|---|
| Oli1 | AA<u>GGATCC</u>AGACCTCGACCACCGGTG | For amplification of homology arm A |
| Oli2 | AA<u>CTCGAG</u>CACGATTTCCAGCGCATG | For amplification of homology arm A |
| Oli3 | AA<u>ACTAGT</u>CTCACCCGCTCGCCTTC | For amplification of homology arm B |
| Oli4 | AA<u>ATGCAT</u>TGAGCCACCACGGCGTG | For amplification of homology arm B |
| Oli5 | GCAGAAGGAACCGCGCAC | For cassette insertion analysis |
| Oli6 | CGATTGTCTGTTGTGCCCAGTC | For cassette insertion analysis |
| Oli7 | GGCTGACCGCTTCCTCGTG | For cassette insertion analysis |
| Oli8 | CGCACCCTGGAGTCGGAC | For cassette insertion analysis |

(Restriction sites engineered for cloning are underlined)

Disruption cassette assembly. The ahba-b disruption cassette was assembled in one step into the pKC1139 conjugative plasmid (Bierman et al., Gene 1992, 116 (1), 43-9) by making a four piece ligation of the following DNA fragments: upstream arm PCR product digested with BamHI-XhoI, the kanamycin resistance cassette from pFDneoS (Denis et al., Gene 1992, 111 (1), 115-8) digested with XhoI-NsiI, downstream arm PCR product digested with NsiI-SpeI and pKC1139 vector digested with BamHI-SpeI. The obtained plasmid was named pKOS554-106 and its structure was confirmed by sequencing. Plasmid pKOS554-106 contained fragments of the genes ahba-3 and ahba-1 flanking a kanamycin resistance cassette (Km$^R$), an apramycin resistance marker (Apra$^R$), and the psG5 thermosensitive origin of replication (ori), as shown in FIG. 1.

E. coli-S. hyoroscopicus conjugation. Plasmid pKOS554-106 was introduced into S. hygroscopicus var. geldanus NRRL 3602 by conjugation as described in Kieser, supra, using E. coli ET12657/pUZ8002 as the donor. Primary exconjugants were grown in 5 mL of R5 liquid medium (Kieser, supra) containing kanamycin (50 mg/L) at 30° C. for 2 days. To select the mutants, 0.2 mL of these cells were used to inoculate 5 mL of R5 with kanamycin and grown for 2 days at 37° C. This step was repeated once and cells were diluted and plated on tomato agar plates and incubated at 28° C. for 14 days. Individual colonies with double crossover were identified by the lack of apramycin resistance by replica plating onto R5 plates supplemented with apramycin (100 mg/L).

Confirmation of insertional disruption by genetic analysis. Colonies (kanamycin resistant and apramycin sensitive) were grown on liquid R5 and genomic DNA was obtained as described in Kieser. PCR analysis using the primer pairs Oli5/Oli6 and Oli7/Oli8 (Table 1 and FIG. 1) was carried out using PCR fail-safe kit to confirm the insertional disruption.

Strain K554-161 and geldanamycin production. FIG. 2 shows the LC-MS trace for the product isolate from a fermentation of strain K554-161 alone (without any added AHBA). Geldanamycin, if produced, should have eluted in just less than 10 min under the HPLC conditions employed. As the figure shows, no geldanamycin was produced. FIG. 3a shows the LC-MS trace of the product isolate when strain K554-161 was fermented in the presence of 1 mM AHBA. There was a large elution peak at 9.96 min, where geldanamycin was expected to elute. FIG. 3b is the mass spectrum of the 9.96 min material, confirming its identity as geldanamycin (the calculated m/z for geldanamycin is 559.3 [M-H]$^-$). FIGS. 4a and 4b are respectively the LC-MS trace and mass spectrum (for the material eluting at 9.97 min) for the product isolate from a control experiment in which the natural geldanamycin-producing organism S. hygroscopicus NRRL 3602 was fermented. The production of geldanamycin is clearly demonstrated by FIGS. 4a and 4b.

EXAMPLE 2

3-Amino-5-chlorobenzoic Acid

The hydrochloride salt of replacement starter unit 3-amino-5-chlorobenzoic acid was prepared as shown below:

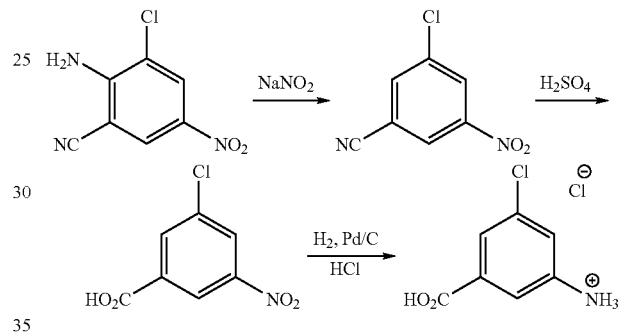

3-Chloro-5-nitrobenzonitrile. Concentrated $H_2SO_4$ (440 mL) was added slowly to crushed ice (1200 g) and 2-amino-3-chloro-5-nitrobenzonitrile (43.8 g) was suspended in the resulting $H_2SO_4$ solution. After addition of 2-propanol (1600 mL), the mixture was heated to 40° C. internal temperature with vigorous stirring. A solution of $NaNO_2$ (66.0 g) in water (100 mL) was added dropwise. After completion of addition, the mixture was kept at 40° C. for an additional 3 h, then cooled to ambient temperature and extracted with $CH_2Cl_2$. The organic extract was washed sequentially with water, 0.1 N NaOH, water, and brine, and then dried over $MgSO_4$, filtered through a pad of silica gel, and evaporated to yield the crude product as a yellow solid. Chromatography on silica gel (20% EtOAc/hexanes) followed by crystallization from 2-propanol yielded the product as yellow crystals. $^1$H-NMR ($CDCl_3$): δ 8.47 (1H, t, J=2.0 Hz), 8.43 (1H, dd, J=1.4, 2.0 Hz), 7.98 (1H, dd, J=1.4, 2.0 Hz). $^{13}$C-NMR ($CDCl_3$): δ 148.8, 137.4, 137.0, 128.1, 125.3, 115.4, 115.3.

3-Chloro-5-nitrobenzoic acid. 3-Chloro-5-nitrobenzonitrile (30.0 g) was dissolved in a mixture of water (85 mL) and $H_2SO_4$ (250 mL) and heated under an $N_2$ atmosphere at 150° C. for 2 h. The mixture was cooled to ambient temperature and poured onto ice (1 L). The resulting solid was collected by vacuum filtration, and the filtrate was extracted with ethyl acetate. The extract and solid were combined, washed with water and brine, then were dried over $MgSO_4$, filtered, and evaporated. The residue was dissolved in 1:1 water/MeOH (200 mL) with heating, treated with decolorizing charcoal and filtered. Water (100 mL) was added and the mixture was allowed to cool and crystallize. The product was obtained as pale yellow crystals. $^1$H-NMR ($d_6$-DMSO): δ 14.00 (1H, br s), 8.51 (2H, m), 8.29 (1H, m). $^{13}$C-NMR (d$_6$-DMSO): δ 164.9, 149.2, 135.2, 135.0, 134.5, 127.7, 122.9.

3-Amino-5-chlorobenzoic acid hydrochloride. A mixture of 3-chloro-5-nitrobenzoic acid (10.0 g) and 10% Pd/C (0.3 g) in MeOH (100 mL) and 6N HCl (30 mL) was shaken under 30 psi H$_2$ in a Parr apparatus for 30 min, then filtered through Celite and evaporated. The residue was crystallized from 6N HCl to yield the product. More highly purified material was obtained by a second crystallization from water. $^1$H-NMR (d$_4$-CD$_3$OD): δ 7.24 (1H, dd, J=1.4, 2.0 Hz), 7.20 (1H, dd, J=1.6, 2.0 Hz), 6.87 (1H, t, J=2.0 Hz). $^{13}$C-NMR (d$_4$-CD$_3$OD): δ 167.6, 149.5, 134.3, 132.7, 117.8, 117.4, 113.9.

EXAMPLE 3

3-Amino-5-fluorobenzoic Acid

The hydrochloride salt of replacement starter unit 3-amino-5-fluorobenzoic acid was prepared as follows:

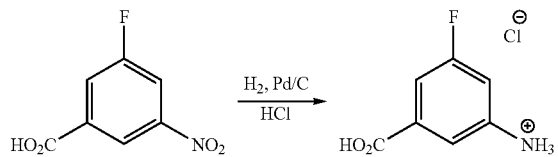

A mixture of 3-fluoro-5-nitrobenzoic acid (5.0 g) and 10% Pd/C (0.3 g) in MeOH (100 mL) and 6 N HCl (20 mL) was shaken under 30 psi H$_2$ for 30 min. The catalyst was removed by filtration, and the solution was evaporated to dryness. The residue was crystallized from 6 N HCl to yield the product. $^{13}$C-NMR (D$_2$O): δ 167.6, 162.5 (d, J$_{CF}$=246 Hz), 133.8 (d, J$_{CF}$=8 Hz), 132.6 (d, J$_{CF}$=10 Hz), 119.7 (d, J$_{CF}$=3 Hz), 116.7 (d, J$_{CF}$=23 Hz), 115.2 (d, J$_{CF}$=24 Hz).

EXAMPLE 4

3-Amino-6-fluorobenzoic Acid

The hydrochloride salt of replacement starter unit 3-amino-6-fluorobenzoic acid was prepared as follows:

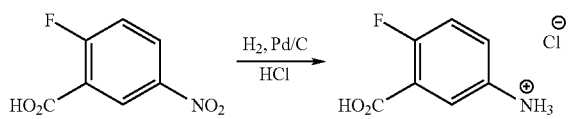

A solution of 2-fluoro-5-nitrobenzoic acid (5.0 g) in MeOH (100 mL) and 6 N HCl (15 mL) was shaken with 0.15 g of 10% Pd/C under 30 psi H$_2$ for 30 min. The catalyst was removed by filtration, and the filtrate was evaporated. The residue was crystallized from 6N HCl to provide the product. $^1$H-NMR (D$_2$O): δ 7.82 (1H, dd, J=2.8, 6.0 Hz), 7.55 (1H, ddd, J=2.8, 4.0, 8.9 Hz), 7.27 (1H, dd, J=8.9, 14.0 Hz). $^{13}$C-NMR (D$_2$O): δ 166.5 (d, J$_{CF}$=2 Hz), 161.3 (d, J$_{CF}$=260 Hz), 129.7 (d, J$_{CF}$=10 Hz), 126.6, 126.0 (d, J$_{CF}$=3 Hz), 120.0 (d, J$_{CF}$=11 Hz), 118.9 (d, J$_{CF}$=25 Hz).

EXAMPLE 5

3-Amino-4-fluorobenzoic Acid

The hydrochloride salt of replacement starter unit 3-amino-4-fluorobenzoic acid was prepared as follows:

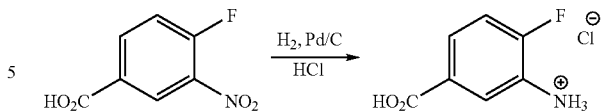

A solution of 4-fluoro-5-nitrobenzoic acid (5.0 g) in MeOH (100 mL) and 6 N HCl (15 mL) was shaken with 0.15 g of 10% Pd/C under 30 psi H$_2$ for 30 min. The catalyst was removed by filtration, and the filtrate was evaporated. The residue was crystallized from 6N HCl to provide the product. $^1$H-NMR (D$_2$O): δ 7.89 (2H, m), 7.25 (1H, t, J=10 Hz).

EXAMPLE 6

3-Amino-2-fluorobenzoic Acid

The trifluoroacetate salt of replacement starter unit 3-amino-2-fluorobenzoic acid was prepared as follows:

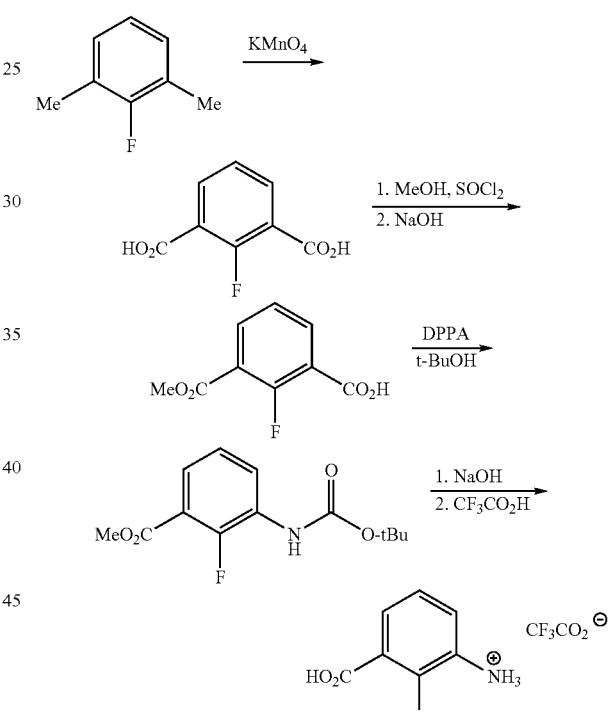

2-Fluoroisophthalic acid. A mixture of 1,3-dimethyl-2-fluorobenzene (4 g) in water (75 mL) was treated with KMnO$_4$ (11.0 g), and the dark purple mixture was slowly heated to reflux. After 12 h at reflux, the mixture was cooled and vacuum filtered through a pad of Celite. The colorless filtrate was acidified to pH 1, whereupon the product crystallized. Vacuum filtration provided the product. $^1$H-NMR (CD$_3$OD/CDCl$_3$): δ 8.10 (2H, dd, J=6.4, 7.6 Hz), 7.31 (1H, t, J=7.6 Hz). $^{13}$C-NMR (CD$_3$OD/CDCl$_3$): δ 165.5, 161.1 (d, J$_{CF}$=271 Hz), 136.1, 123.4 (d, J$_{CF}$=5 Hz), 120.6 (d, J$_{CF}$=11 Hz).

Monomethyl 2-fluoroisophthalate. 2-Fluoroisophthalic acid was dissolved in MeOH (100 mL), cooled to −10° C., and treated dropwise with SOCl$_2$ (5 mL). After completion of addition, the mixture was warmed to ambient temperature and stirred overnight, then evaporated to dryness. The residue was dissolved in EtOAc, washed with saturated aqueous NaHCO₃, dried over MgSO₄, filtered, and evaporated to yield the dimethyl ester. The dimethyl ester was dissolved in MeOH (50 mL) and treated with 1.0 molar equivalent of 5N NaOH overnight at ambient temperature. The mixture was concentrated and the residue was partitioned between water and CH₂Cl₂. The aqueous phase was acidified with 6N HCl, and the resulting precipitate was collected by filtration and air dried to yield the product. ¹H-NMR (CD₃OD): δ 8.10 (2H, m), 7.34 (1H, t, J=8.0 Hz), 3.93 (3H, s).

Methyl 3-(tert-butoxycarbonylamino)-2-fluorobenzoate. A solution of monomethyl 2-fluoroisophthalate (0.4 g) in tert-butyl alcohol (10 mL) was treated with Et₃N (0.56 mL) and diphenylphosphoryl azide (0.75 mL). After 1 h, the mixture was heated at reflux for 24 h, then cooled and concentrated. The residue was diluted with EtOAc, washed with saturated aqueous NaHCO₃, dried over MgSO₄, filtered, and evaporated. Silica gel chromatography (acetone/hexane gradient) provided the product. ¹H-NMR (CDCl₃): δ 8.31 (1H, br t, J=7.2 Hz), 7.55 (1H, ddd, J=1.6, 6.8, 8.0 Hz), 7.16 (1H, ddd, J=1.2, 8.0, 8.0 Hz), 6.80 (1H, br s), 3.93 (3H, s), 1.54 (9H, s).

3-Amino-2-fluorobenzoic acid trifluoroacetate salt. A mixture of the methyl 3-(tert-butoxycarbonylamino)-2-fluorobenzoate in 1 N NaOH was stirred for 2 h at ambient temperature, then acidified and extracted with ethyl acetate. The extract was dried over MgSO₄, filtered, and evaporated. The residue was dissolved in 5 mL of trifluoroacetic acid, kept for 10 minutes, and then evaporated to dryness to provide the product. ¹H-NMR (D₂O): δ 7.80 (1H, ddd, J=1.6, 8.0, 8.0 Hz), 7.54 (1H, ddd, J=1.2, 4.0, 4.0 Hz), 7.28 (1H, t, J=8.0 Hz). ¹³C-NMR (D₂O): δ 167.2, 154.1 (d, J_{CF}=257 Hz), 130.2, 127.9, 124.9, 122.5, 120.1.

EXAMPLE 7

3-Amino-5-methoxybenzoic Acid

The hydrochloride salt of replacement starter unit 3-amino-5-methoxybenzoic acid was prepared as follows:

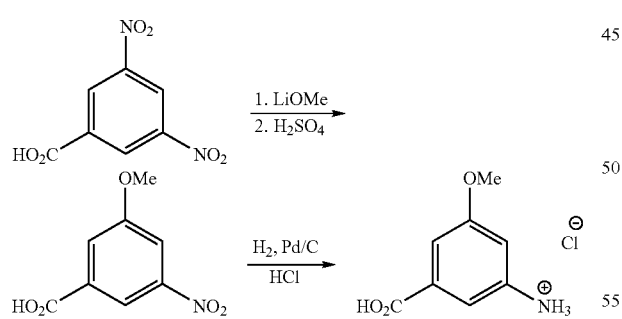

3-Methoxy-5-nitrobenzoic acid. 3,5-Dinitrobenzoic acid (866 mg) was dissolved in 1 M LiOMe in MeOH (1.3 mL), then evaporated to dryness. The resulting solid was dissolved in 30 mL of hexamethyl phosphoramide and heated at 80° C. for 16 h. The mixture was then cooled and poured onto a mixture of crushed ice (250 g) and 6NH₂SO₄ (42 mL). The mixture was extracted with ether, and the extract was washed with water and brine, then dried over MgSO₄, filtered and evaporated to yield an orange solid. Filtration through silica gel using 9:1 CH₂Cl₂/MeOH followed by evaporation provided 624 mg of product. ¹H-NMR (d₆-acetone): δ 8.36 (1H, dd, J=1.6, 2.0 Hz), 7.97 (1H, t, J=2.0 Hz), 7.91 (1H, dd, J=1.6, 2.0 Hz), 4.03 (3H, s).

3-Amino-5-methoxybenzoic acid hydrochloride. The product from above was dissolved in MeOH (20 mL) and treated with 6 N HCl (2 mL) and 10% Pd/C (50 mg) under an H₂ atmosphere for 30 min. The catalyst was removed by filtration, and the mixture was evaporated to dryness. The product was obtained by crystallization from 6N HCl. ¹H-NMR (D₂O): δ 7.43 (1H, dd, J=1.3, 2.5 Hz), 7.40 (1H, dd, J=1.3, 2.0 Hz), 7.02 (1H, t, J=2.2 Hz), 3.72 (3H, s). ¹³C-NMR (D₂O): δ 168.6, 160.1, 133.0, 131.6, 116.0, 115.1, 113.6, 55.8.

EXAMPLE 8

3-Amino-5-chloro-4-hydroxybenzoic Acid

The hydrochloride salt of the replacement starter unit 3-amino-5-chloro-4-hydroxybenzoic acid was prepared as follows:

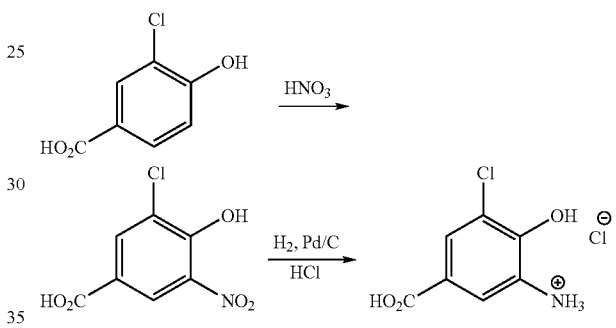

3-chloro-4-hydroxybenzoic acid (5.0 g) was added in small portions to stirred fuming HNO₃ (90%, 15 mL) cooled on ice. After completion of addition, the orange mixture was allowed to warm to 20° C. and stirring was continued for 2 h. Ice water (50 mL) was added, and the precipitated product was collected by vacuum filtration to yield 5.4 g of 3-chloro-4-hydroxy-5-nitrobenzoic acid as a bright yellow solid.

A mixture of 3-chloro-4-hydroxy-5-nitrobenzoic acid (5 g) and 10% palladium/carbon (0.1 g) in methanol (100 mL) and 6N HCl (20 mL) was shaken under 30 psi of hydrogen for 30 minutes using a Parr shaker. The catalyst was removed by filtration, and the solution was evaporated to dryness. The product was crystallized from 6N HCl. ¹H-NMR (400 MHz, D₂O): δ 7.78 (1H, d, J=3 Hz), 7.71 (1H, d, J=3 Hz). ¹³C-NMR (100 MHz, D₂O): δ 167.7, 150.6, 131.4, 123.8, 122.4, 121.5, 120.3.

EXAMPLE 9

Preparation of Inoculum for Production of Macrolactams

Seed cultures were prepared by inoculating 1 mL spore suspension of strain K554-161 strain (10⁸ spores) into 50 mL of YPD broth (Sigma) and incubated with agitation at 28° C. in a 250 mL Erlenmeyer flask for 24 h. Five mL of this culture were used to inoculate 40 mL of Modified DeBoer Beet Molasses Medium (glucose (Sigma), 36.4 g/L; wheat peptone E1 (Organotechnie), 5 g/L; soy peptone type SL (Marcor), 5 g/L; bacto yeast extract (BD), 2.5 g/L; oatmeal (Gerber), 5 g/L; beet molasses (Minn-Dak), 10 g/L equilibrated to pH 7 with NaOH) in a 250 mL baffled Erlenmeyer flask. Replacement starter units dissolved in DMSO (100 mM) were added to obtain a 1 mM concentration. Cultures were incubated at 28° C. with agitation until ansamycin production leveled. Cultures supplemented with AHBA, with no precursor and cultures of the wild type strain were prepared as controls in all the experiments.

One milliliter of frozen spores of strain K554-161 in 20% (v/v) glycerol was inoculated into 50 mL of filter-sterilized YSD medium, consisting of 10 g/L Bacto yeast extract (BD), 20 g/L soy peptone type SL (Marcor), and 20 g/L glucose, in a 250-mL baffled Erlenmeyer flask. The cells were incubated at 28° C. and 190 rpm on a rotary shaker with a 2-inch stroke for 22-24 h. Secondary seed cultures were generated by transferring 22.5 mL of the primary seed culture into 2.8-L baffled Fernbach flasks containing 450 mL of YSD medium. These cultures were grown at 28° C. and 190 RPM for 16-18 h.

EXAMPLE 10

Preparation and Isolation of Macrolactams Without use of XAD-16HP Resin

The following is a representative procedure using 3-amino-5-chlorobenzoic acid or 3-amino-5-fluorobenzoic acid as a replacement starter unit. Preparations with other replacement starter units can be analogously performed. Later herein, an alternative preparation in the presence of a resin such as XAD-16HP will be described.

Fermentation. Five-liter bioreactors (B. Braun) containing 4.5 L of Modified DeBoer Beet Molasses Medium were autoclaved at 121° C. for 60 min. They were then inoculated with 225 mL of secondary seed culture. The fermentations were performed at 28° C. with an aeration rate of 0.4 v/vim and an initial agitation rate of 400 rpm. The dissolved oxygen was controlled at 30% of air saturation by an agitation cascade between 400-1000 rpm. The culture pH was maintained at 7.0 with the automatic addition of 2.5 N sulfuric acid or 2.5 N sodium hydroxide. Foaming was controlled by the automatic addition of 100% UCON LB-625. The replacement starter units were prepared as concentrated 1 M solutions in DMSO. They were added to the production cultures one day after inoculation to a final concentration of 0.5 mM. The fermentations were grown for four days.

Isolation of compound III-a. Ten liters of fermentation broth with the use of 3-amino-5-chlorobenzoic acid as the replacement starter unit were extracted with an equal volume of methanol for 2 h and filtered. The filtrate was chromatographed on 1.2 L of HP-20SS sorbent (Supelco) with a step gradient (2.5 column volume (CV) of 40:60 (v/v) methanol:water, 2.5 CV of 50:50 (v/v) methanol:water, 2.5 CV of 60:40 (v/v) methanol:water, and 2.5 CV of 100% methanol). The fractions containing the target compound by LC-MS (m/z=551 [M-H]$^-$) were combined and chromatographed on 1.0 L of $C_{18}$ sorbent (Bakerbond, 40 µm) with a step gradient (4 CV of 50:50 (v/v) methanol:water, 4 CV of 55:45 (v/v) methanol:water, 4 CV of 60:40 (v/v) methanol:water, and 4 CV of 65:35 (v/v) methanol:water). The fractions containing the target compound III-a by LC-MS were combined and further purified by $C_{18}$ chromatography in 30:70 (v/v) acetonitrile:water on the same $C_{18}$ process column. The remaining minor impurities in the enriched product pool were separated by preparative HPLC (Inertsil ODS-3, 8 µm, 250 mm×300 mm) in 30:70 (v/v) acetonitrile:water. A total of 52 mg of compound III-a was isolated as a pale yellow solid.

Isolation of compound III-d. Nine liters of fermentation broth with the use of 3-amino-5-fluorobenzoic acid as the replacement starter unit were sedimented by centrifugation. The supernatant was chromatographed on 1.0 L of HP-20SS sorbent with a step gradient (3 CV of 40:60 (v/v) methanol:water, 3 CV of 50:50 (v/v) methanol:water, 3 CV of 60:40 (v/v) methanol:water, 3 CV of 70:30 (v/v) methanol:water, and 3 CV of 80:20 (v/v) methanol:water). The fractions containing the target compound by LC-MS (m/z=535 [M-H]$^-$) were combined and further purified on 1.0 L of $C_{18}$ sorbent in 50:50 (v/v) methanol:water. The fractions containing the target compound III-d by LC-MS were combined, and the minor impurities in the enriched product pool were separated by preparative HPLC in 30:70 (v/v) acetonitrile:water. A total of 241 mg of compound III-d was isolated as a pale yellow solid.

Isolation of compound IV-c. Compound IV-c was isolated from the fermentations above that produced III-d (i.e., in the absence of XAD-16HP). Fractions from the $C_{18}$ chromatography and preparative HPLC steps in the purification of compound III-d that contained the target compound IV-c by LC-MS (m/z=533 [M-H]$^-$) were combined. The product pool was purified by preparative HPLC in 27:73 (v/v) acetonitrile:water to yield 1.8 mg of compound IV-c as a yellow solid.

EXAMPLE 11

Preparation of Macrolactams with Use of XAD-16HP Resin

We have discovered that the addition of an adsorbent resin during fermentation improves the yield of the macrolactams. Without being bound by theory, it is believed that the resin adsorbs the macrolactams and protects them from decomposition or degradation.

The adsorbent resin preferably comprises a non-ionic (unfunctionalized), hydrophobic polymer, such as a polystyrene or a styrene-divinylbenzene copolymer. Such resins are highly porous and can reversibly adsorb organic molecules from an aqueous medium. Exemplary suitable resins include the Amberlite™ XAD resins (particularly grades XAD16, XAD-16HP, XAD7, XAD8, XAD1180, and XAD5), the Amberchrom™ resins (particularly grade CG161), the DIAION™ resins (particularly grade HP20) and the SEPABEADS™ resins. Amberlite™ and Amberchrom™ resins are available from Rohm & Haas while the DIAION™ and the SEPABEADS™ resins are available from Mitsubishi Chemical. The resin preferably is XAD-16HP. Those skilled in the art will appreciate that it may be desirable to empirically determine the desired type and amount of resin.

Fermentation. A 1-L flask containing 90 g of XAD-16HP (Rohm & Haas) and 200 mL of deionized water was attached to each 5-L bioreactor using a long piece of ½" silicone tubing that was clamped prior to sterilization. The bioreactors contained 4.5 L of Modified DeBoer Beet Molasses Medium and were autoclaved at 121° C. for 60 min. After sterilization, the silicone tubings were unclamped, and the resin was added to the production medium. The bioreactors were then inoculated with 225 mL of secondary seed culture. These fermentations were performed under same conditions as described for the fermentations without the use of the adsorber resin.

Isolation of compound III-a. Thirty-eight liters of fermentation broth with the use of 3-amino-5-chlorobenzoic acid as the replacement starter unit were sedimented by centrifugation. The supernatant was decanted, and the XAD-16HP resin and cell pellet were extracted with 10 L of 100% methanol. The extraction mixture was filtered, and the filtrate was chromatographed on 1.75 L of HP-20SS sorbent with a step gradient (3 CV of 40:60 (v/v) methanol:water, 3 CV of 50:50 (v/v) methanol:water, 3 CV of 60:40 (v/v) methanol:water, 3

CV of 70:30 (v/v) methanol:water, and 3 CV of 80:20 (v/v) methanol:water). The fractions that contained compound III-a were combined and chromatographed on 1.0 L of $C_{18}$ sorbent in 45:55 (v/v) methanol:water. The enriched fractions were further purified on 400 mL of $C_{18}$ sorbent in 30:70 (v/v) acetonitrile:water to yield 357 mg of compound III-a as a yellow solid.

Isolation of compound III-d. Nine liters of fermentation broth with the use of 3-amino-5-fluorobenzoic acid as the replacement starter unit were sedimented by centrifugation. The supernatant was decanted and set aside. The XAD-16HP resin and cell pellet were extracted with 9 L of methanol and filtered. The filtrate and supernatant were then combined and chromatographed on 1.5 L of HP-20SS sorbent with a step gradient (3 CV of 40:60 (v/v) methanol:water, 3 CV of 50:50 (v/v) methanol:water, 3 CV of 60:40 (v/v) methanol:water, and 3 CV of 70:30 (v/v) methanol:water). The fractions that contained compound III-d were combined and chromatographed on 1.0 L of $C_{18}$ sorbent in 50:50 (v/v) methanol:water. The enriched fractions were further purified on 400 ml of $C_{18}$ sorbent in 27:73 (v/v) acetonitrile:water to yield 1.3 g of compound III-d as a yellow solid.

Isolation of compound IV-b. Compound IV-b was isolated from the fermentations that produced compound III-a in the presence of XAD-16HP (above). Fractions from the first $C_{18}$ chromatography step in the purification of compound III-a which contained the target compound IV-b by LC-MS (m/z=565 [M-H]$^-$) were combined. The product pool was chromatographed on 400 mL of $C_{18}$ sorbent in 42:58 (v/v) methanol:water. The enriched fractions were further purified by preparative HPLC in 27:73 (v/v) acetonitrile:water to yield 23 mg of compound IV-b as a yellow solid.

EXAMPLE 12

Characterization of Macrolactams

Most of the time, the feeding of a replacement starter unit to strain K554-161 resulted in the production of a mixture of macrolactams, as summarized in Table 2. (In some instances, as noted in Table 2, the replacement starter unit was a commercially available material.)

TABLE 2

Macrolactams Produced by Feeding of Replacement Starter Units

| Replacement Starter Unit | Macrolactam(s) produced |
| --- | --- |
| 3-Amino-5-chlorobenzoic acid | III-a (major product), III-b, III-c, IV-b |
| 3-Amino-5-fluorobenzoic acid | III-d (major product), III-e, III-f, IV-c |
| 3-Amino-5-methoxybenzoic acid | III-g |
| 3-Aminobenzoic acid (a) | III-h, III-i, IVa |
| 3-Amino-2-chlorobenzoic acid (a) | III-j |
| 3-Amino-2-fluorobenzoic acid | III-k |
| 3-Amino-4-fluorobenzoic acid | III-l, III-m |
| 3-Amino-6-fluorobenzoic acid | III-n, III-o |
| 3-Amino-4-hydroxybenzoic acid (a) | III-p, IV-d |
| 3-Amino-5-chloro-4-hydroxybenzoic acid | III-q |

(a) Commercially available compound

The analytical characteristics of macrolactams produced are given below:

Compound III-a. $^1$H NMR (400 MHz, THF-d$_8$, 320 K) δ 8.44 (1H, s), 7.68 (very br s), 7.42 (1H, br s), 6.76 (1H, d, J=2.5 Hz), 5.87 (1H, t, J=6.5 Hz), 5.75 (2H, br s), 5.31 (1H, d, J=10.0 Hz), 5.06 (1H, d, J=6.0 Hz), 3.52 (1H, dd, J=7.0, 4.0), 3.35 (3H, s), 3.32 (3H, s), 3.31 (1H, m), 3.13 (1H, dt, J=8.0, 4.0 Hz), 2.80 (1H, dd, J=14.0, 5.5 Hz), 2.48 (1H, dqd, J=10.0, 7.0, 6.5 Hz), 2.44 (1H, dd, J=14.0, 5.5 Hz), 2.31 (1H, m), 2.15 (1H, m), 1.96 (1H, m), 1.80 (3H, s), 1.68 (1H, m), 1.50 (3H, s), 1.40 (2H, m), 1.21 (1H, m), 0.99 (3H, d, J=6.5 Hz), 0.88 (3H, d, J=7.0 Hz). $^{13}$C NMR (100 MHz, THF-d$_8$, 320 K) δ 170.7, 157.3, 148.6, 134.7, 133.5, 133.4, 132.7, 131.5, 130.2, 125.5, 120.8, 120.4, 82.6, 81.4, 80.9, 75.1, 58.7, 57.0, 37.1, 35.3, 34.6, 32.4, 30.9, 25.2, 19.8, 17.0, 13.4, 12.9. HR-ESI-MS m/z 575.2479 [M+Na]$^+$; calcd for $C_{28}H_{41}O_7{}^{35}ClN_2Na$, 575.2495.

Compound III-b. ESI-MS m/z 567.3; calcd for $C_{28}H_{40}{}^{35}ClN_2O_8$ [M-H]$^-$: 567.3.

Compound III-c. ESI-MS m/z 551.3; calcd for $C_{28}H_{40}{}^{35}ClN_2O_7$ [M-H]$^-$: 551.3.

Compound III-d. $^1$H NMR (400 MHz, THF-d$_8$, 330K) δ 8.39 (1H, s), 7.96 (1H, d, J=1.0 Hz), 7.25 (1H, d, $^3J_{H-F}$=11.5 Hz), 6.63 (1H, s), 5.92 (1H, br t, J=7.0 Hz), 5.70 (2H, br s), 5.35 (1H, d, J=10.0 Hz), 5.08 (1H, d, J=5.5 Hz), 3.51 (1H, dt, J=7.0, 4.0 Hz) 3.35 (3H, s), 3.32 (3H, s), 3.32 (1H, m), 3.17 (1H, d, J=4.0 Hz, exchangeable), 3.15 (1H, dt, J=8.0, 4.0 Hz), 2.75 (1H, dd, J=14.0, 6.0 Hz), 2.50 (1H, dqd, J=10.0, 7.0, 6.5 Hz), 2.44 (1H, dd, J=14.0, 6.0), 2.32 (1H, m), 2.17 (1H, m), 1.92 (1H, dqtd, J=7.5, 7.0, 6.0, 5.5 Hz), 1.79 (3H, d, J=1.0 Hz), 1.66 (1H, ddd, J=14.0, 8.0, 5.5 Hz), 1.53 (3H, d, J=1.5 Hz), 1.47 (2H, m), 1.29 (1H, ddd, J=14.0, 7.5, 4.0 Hz), 0.99 (3H, d, J=6.5 Hz), 0.89 (3H, d, J=7.0 Hz); $^{13}$C NMR (100 MHz, THF-d$_8$, 335 K) δ 170.5, 157.3, 152.2 (d, $J_{C-F}$=235 Hz), 140.5 (d, $J_{C-F}$=15 Hz), 134.5, 133.9 (br), 132.9, 132.4 ($J_{C-F}$=11 Hz), 120.9 (br), 131.6, 131.0, 107.2 ($J_{C-F}$=23 Hz), 82.9, 81.6, 80.9, 75.4, 58.6, 57.1, 36.4, 35.2, 35.1, 32.7, 30.9, 25.3, 20.2, 16.7, 13.3, 12.9 HR-ESI-MS m/z 559.2806 [M+Na]$^+$; calcd for $C_{28}H_{40}O_7FN_2Na$, 559.2790.

Compound III-e. ESI-MS m/z 551.3; calcd for $C_{28}H_{40}FN_2O_8$ [M-H]$^-$: 551.3.

Compound III-f ESI-MS m/z 535.3; calcd for $C_{28}H_{40}FN_2O_7$ [M-H]$^-$: 535.3.

Compound III-g. ESI-MS m/z 531.3; calcd for $C_{29}H_{43}N_2O_7$[M-H]$^-$: 531.3.

Compound III-h. HR-ESI-MS m/z 525.2950; calcd for $C_{28}H_{42}N_2O_6Na$ [M+Na]$^+$: 525.2935.

Compound III-i. HR-ESI-MS m/z 541.2880; calcd for $C_{28}H_{42}N_2O_7Na$ [M+Na]$^+$: 541.2884.

Compound III-j. ESI-MS m/z 551.3; calcd for $C_{28}H_{40}{}^{35}ClN_2O_7$ [M-H]$^-$: 551.3.

Compound III-k. ESI-MS m/z 535.3; calcd for $C_{28}H_{40}FN_2O_7$ [M-H]$^-$: 535.3.

Compound III-l. ESI-MS m/z 519.3; calcd for $C_{28}H_{40}FN_2O_6$ [M-H]$^-$: 519.3.

Compound III-m. ESI-MS m/z 535.3; calcd for $C_{28}H_{40}FN_2O_7$ [M-H]$^-$: 535.3.

Compound III-n. ESI-MS m/z 535.3; calcd for $C_{28}H_{40}FN_2O_7$ [M-H]$^-$: 535.3.

Compound III-o. ESI-MS m/z 519.3; calcd for $C_{28}H_{40}FN_2O_6$ [M-H]$^-$: 519.3.

Compound III-p. ESI-MS m/z 517.3; calcd for $C_{28}H_{42}N_2O_7$ [M-H]$^-$: 517.3.

Compound III-q. ESI-MS m/z 567.3; calcd for $C_{28}H_{41}ClN_2O_8$ [M-H]$^-$: 567.3.

Compound IV-a. HR-ESI-MS m/z 539.2749; calcd for $C_{28}H_{40}N_2O_7Na$ [M+Na]$^+$: 539.2728.

Compound IV-b. HR-ESI-MS m/z 589.2299; calcd for $C_{28}H_{39}{}^{35}ClN_2O_8Na$ [M+Na]$^+$: 589.2287. $^1$H NMR (400 MHz, THF-d$_8$, 335 K) δ 8.37 (1H, s), 7.98 (1H, br s), 7.72 (1H, br s), 6.97 (1H, br d, J=11.5 Hz), 6.46 (1H, td, J=11.5, 1.5 Hz), 5.8-5.2 (4H, m), 5.00 (1H, d, J=1.5 Hz), 4.34 (1H, d, J=9.5 Hz), 3.35 (1H, m), 3.33 (3H, s), 3.15 (3H, m), 2.85 (1H, dd, J=13.5, 9.0), 2.77 (1H, m), 2.64 (1H, dd, J=13.5, 3.0 Hz), 1.88 (3H, d, <1.0 Hz), 1.88 (1H, overlapped), 1.73 (3H, s), 0.98 (3H, d, J=6.5 Hz), 0.93 (3H, d, J=7.0 Hz). $^{13}$C NMR (100 MHz, THF-d$_8$, 335 K) δ 168.5, 157.3, 147.8, 145.8, 137.2, 134.9, 134.6, 133.3, 127.3, 125.8, 122.7, 118.2, 117.8, 111.6, 82.4, 82.1, 81.9, 75.4, 57.0, 56.5, 36.3, 34.1, 33.7, 30.3, 23.2, 13.1, 12.8, 12.7.

Compound IV-c. ESI-MS m/z 533.3; calcd for C$_{28}$H$_{38}$FN$_2$O$_7$ [M-H]$^-$: 533.3.

Compound IV-d. ESI-MS m/z 515.3; calcd for C$_{28}$H$_{40}$N$_2$O$_7$ [M-H]$^-$: 515.3.

EXAMPLE 13

Inhibition of Cancer Cell Growth

The ability of the macrolactams of this invention to inhibit the growth of cancer cells was evaluated using the procedure of Patel, supra. The results are presented in Table 3. MCF-7, SKBr3, MX-1, BT-474, and NCI/ADR are human breast cancer cell lines, with the latter being multi-drug resistant. SKOV3 is a human ovarian cancer cell line. K-562 is a human leukemia cell line (chronic myelogenous leukemia, or CML). RPMI-8226 is another human leukemia cell line (myeloma). MV-4-11 is yet another human leukemia cell line (acute myeloid leukemia or AML). HCT-116, HT-29, and COLO 205 are a human colon cancer cell lines. For comparison, data for the prior art compounds 17-AAG and 17-DMAG also are included. Where an assay was performed multiple times, the range of values measured is given.

TABLE 3

(Part A) - Inhibitory Activity against Cancer Cells

| Cancer Cell Line | Macrolactam (IC$_{50}$, nM) | | | |
|---|---|---|---|---|
| | 17-AAG | 17-DMAG | III-a | III-d |
| BT-474 | 21 | 17 | 57 | 80 |
| HCT-116 | 99-290 | 47 | 120 | 280-290 |
| K-562 | 230 | 40 | 74 | 290 |
| MX-1 | 58 | 59 | 42 | 66 |
| RPMI-8226 | 63 | 56 | 42 | 66 |
| SKBr3 | 21-151 | 60-77 | 36-145 | 34-80 |
| SKOV3 | 121-332 | 100-190 | 102-170 | 230-237 |
| MCF-7 | 31-100 | 41-91 | 53-60 | 73-160 |
| MV-4-11 | 12-13 | 7-8 | — | 31-32 |
| HT-29 | 31 | 17 | — | 110 |
| COLO 205 | 13 | 4 | — | 38 |
| NCI-ADR | 1,600-3,600 | 1,100-1,600 | 640-1,400 | 3,200-5,000 |

(Part B) - Inhibitory Activity against Cancer Cells

| Cancer Cell Line | Macrolactam (IC$_{50}$, nM) | | | |
|---|---|---|---|---|
| | III-h | III-i | IV-a | IV-b |
| BT-474 | — | — | — | 140 |
| HCT-116 | 240-242 | 1,100 | 177 | 840 |
| K-562 | — | — | — | 1,400 |
| MX-1 | — | — | — | 440 |
| RPMI-8226 | — | — | — | 240 |
| SKBr3 | 90-110 | 830 | 90 | 400-444 |
| SKOV3 | 318 | 840 | 158 | 340-360 |
| MCF-7 | 138-140 | 600 | 87 | 320-340 |
| MV-4-11 | — | — | — | — |
| HT-29 | 220 | — | — | — |
| COLO 205 | 180 | — | — | — |
| NCI-ADR | — | — | — | 10,000 |

The data show that compounds of this invention are bioactive compounds against cancer cells and that, compounds III-a, III-d and IV-b in particular are generally as potent against the cancer cell lines tested as 17-AAG and 17-DMAG.

EXAMPLE 14

Efficacy and NQO1 Activity

As noted above, geldanamycin derivatives in the quinone oxidation state are dependent on the enzyme NQO1 to reduce them to their hydroquinone derivatives for enhanced activity as Hsp90 inhibitors. However, some cancer cells are deficient in NQO1 activity and thus unable to effect the quinone-to-hydroquinone conversion. The macrolactams of this invention are not NQO1-reliant and therefore should be nevertheless effective against such cancer cells. This expectation was confirmed by the results shown in Table 4, where macrolactams III-a, III-d, and IV-b, 17-AAG, and 17-DMAG were compared for inhibitory efficacy against NQO1-deficient breast cancer (MDA-468) and lung cancer (NCI-H596) cells, using the same procedure as in the previous example. As the data show, the macrolactams of this invention are substantially more potent.

TABLE 4

Activity against NQO1 Deficient Cancer Cells

| Compound | Inhibitory Concentration (IC$_{50}$, nM) | |
|---|---|---|
| | MDA-468 | NCI-H596 |
| 17-AAG | 1,600 | 1,600 |
| 17-DMAG | 1,600 | 700 |
| III-a | 90 | 190 |
| III-d | 100 | 310 |
| IV-b | 450 | 815 |

A different experiment leads to the same conclusion. 17-AAG, 17-DMAG, compound III-a, and compound III-d were tested against SKBr3 and MCF7 cancer cells (see Example 12, supra), both of which express NQO1, with and without the addition of dicoumarol, a known inhibitor of NQO1. In the presence of dicoumarol, the Hsp90 inhibitory activities of 17-AAG and 17-DMAG were diminished by about one order of magnitude, while those of compounds III-a and III-d remained substantially unchanged. The results are shown in Table 5.

TABLE 5

Effect of Dicoumarol on Inhibitory Activity

| | Cell Type and Inhibitory Activity (IC$_{50}$, nM) | | | |
|---|---|---|---|---|
| | No dicoumarol added | | Dicoumarol added (50 µM) | |
| Compound | SKBr3 | MCF7 | SKBr3 | MCF7 |
| 17-AAG | 39 | 54 | 410 | 662 |
| 17-DMAG | 36 | 40 | 230 | 882 |
| III-a | 39 | 57 | 54 | 69 |
| III-d | 42 | 112 | 69 | 161 |

Thus, the foregoing results show that compounds of this invention (especially compounds III-a, III-d, and IV-b) are suitable for use in treating hyperproliferative diseases such as cancer, and in particular breast cancer, ovarian cancer, lung cancer, leukemia (especially CML, myeloma and AML), and colon cancer.

EXAMPLE 15

Effect on Client Proteins

The activity of macrolactams of this invention as Hsp90 inhibitors was confirmed by monitoring the effect of exposure to them on an Hsp90 client protein and a protein induced upon Hsp90 inhibition. The results when SKBr3 breast cancer cells were continuously exposed to 1 µM test compound are presented in FIG. 5, with 17-AAG as a reference. The procedure used was that described in Munster et al., *Cancer Research* 2002, 62, 3132-3137.

ErbB2 protein is an Hsp90 client protein and, as such, is indirectly inhibited upon Hsp90 inhibition (Schnur et al., *J. Med. Chem.* 1995, 38 (19), 3813-3820). The top gel picture in FIG. 5 shows that, like 17-AAG, macrolactams III-a and III-d inhibited ErbB2. Heat shock protein-70 ("Hsp70"), another protein that performs a chaperone function, is a protein that is induced upon inhibition of Hsp90 (Brodsky & Chiosis, *Curr. Topics Med. Chem.* 2006, 6 (11), 1215-1225). Thus, the induction of Hsp70 can be used as a marker for the inhibition of Hsp90. The middle gel picture in FIG. 5 shows that Hsp70 was induced by macrolactams III-a and III-d, just as it was by 17-AAG. Thus, the macrolactams of this invention clearly have the same mechanism of action as the known Hsp90 inhibitor 17-AAG. (The third row shows the concentration of glyceraldehyde-3-phosphate dehydrogenase (GAPDH). GAPDH is an enzyme involved in glycolysis and is expressed constitutively in all cells and is a marker of choice as a loading control in Western Blotting experiments.)

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

We claim:

1. A compound having a structure represented by formula III-a:

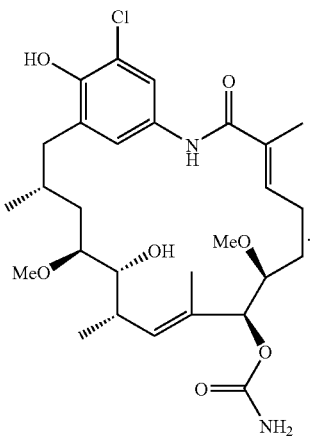

(III-a)

2. A compound having a structure represented by formula III-d

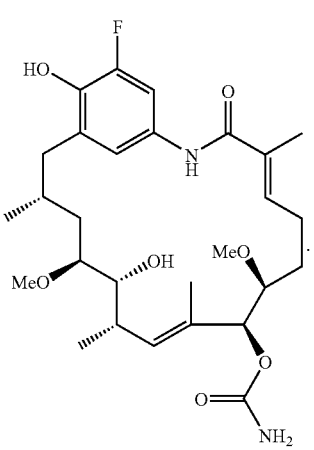

(III-d)

3. A compound having a structure represented by formula IV-a, IV-b, or IV-c:

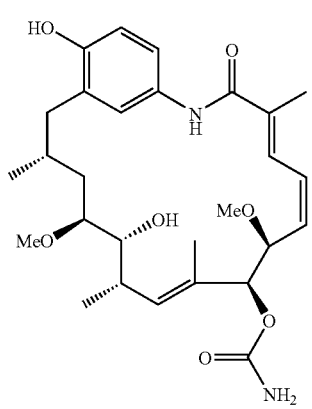

(IV-a)

-continued (IV-b)

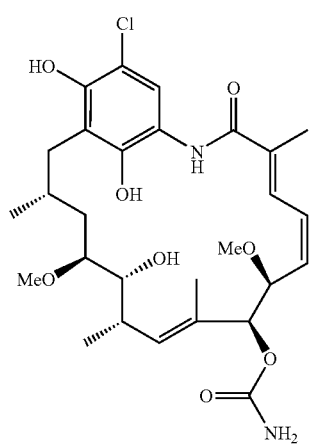

(IV-c)

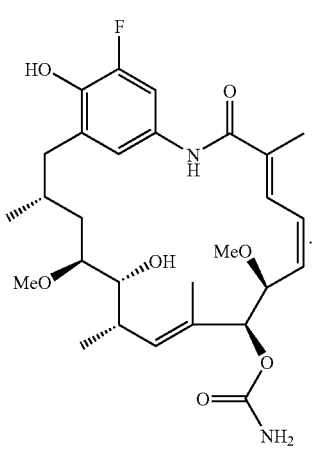

4. A method for treating a hyperproliferative disease wherein the hyperproliferative disease is breast cancer, ovarian cancer, leukemia, colon cancer, or lung cancer in a patient suffering from said disease, comprising administering to said patient a therapeutically effective amount of a compound represented by formula III-a or formula III-d.

5. The method according to claim 4, wherein the compound has a structure represented by formula III-a:

(III-a)

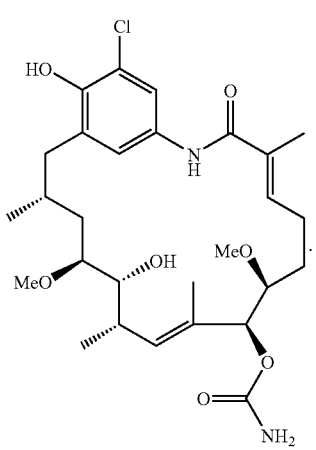

6. The method according to claim 4, wherein the compound has a structure represented by formula III-d:

(III-d)

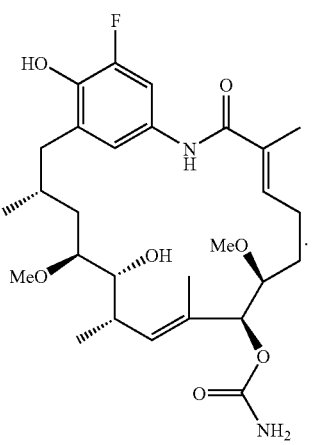

7. A pharmaceutical composition comprising a compound represented by formula III a and a pharmaceutically acceptable excipient.

8. A pharmaceutical composition wherein the compound has a structure represented by formula III-d:

(III-d)

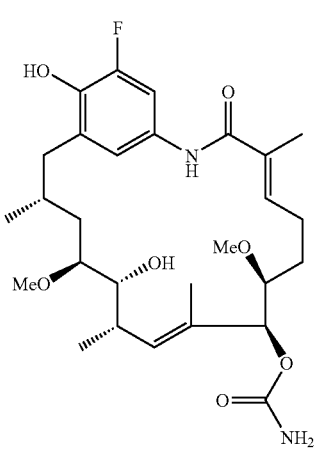

and a pharmaceutically acceptable excipient.

* * * * *

UNITED STATES PATENT AND TRADEMARK OFFICE
CERTIFICATE OF CORRECTION

| | |
|---|---|
| PATENT NO. | : 7,855,192 B2 |
| APPLICATION NO. | : 12/011068 |
| DATED | : December 21, 2010 |
| INVENTOR(S) | : G. Ashley et al. |

It is certified that error appears in the above-identified patent and that said Letters Patent is hereby corrected as shown below:

On the Title Page, item (56), Column 2, Line 21 reads:

"Isaacs, Camcer Cell (2003)3: 213-7." Please delete "Camcer" and insert -- Cancer --

Column 38, Line 26:

In Claim 2, delete "III-d" and insert -- III-d: --

Column 40, Line 32:

In Claim 7, delete "III a" and insert -- III-a --

Signed and Sealed this
Thirtieth Day of August, 2011

David J. Kappos
*Director of the United States Patent and Trademark Office*